United States Patent [19]
Cheronis et al.

[11] Patent Number: 6,075,120
[45] Date of Patent: Jun. 13, 2000

[54] BRADYKININ ANTAGONIST

[75] Inventors: John C. Cheronis, Lakewood; James K. Blodgett, Broomfield; Val Smith Goodfellow; Manoj Vinayak Marathe, both of Westminster; Lyle W. Spruce, Arvada; Eric T. Whalley, Golden, all of Colo.

[73] Assignee: Cortech, Inc., Denver, Colo.

[21] Appl. No.: 08/440,338

[22] Filed: May 12, 1995

Related U.S. Application Data

[63] Continuation of application No. 08/296,185, Aug. 29, 1994, which is a continuation of application No. 07/974,000, Nov. 10, 1992, abandoned, which is a continuation-in-part of application No. 07/859,582, Mar. 27, 1992, abandoned, which is a continuation-in-part of application No. 07/677,391, Apr. 1, 1991, abandoned.

[51] Int. Cl.⁷ .............................. C07K 7/18; A61K 38/08
[52] U.S. Cl. .......................... 530/314; 530/328; 530/402; 514/15; 514/2
[58] Field of Search ................... 514/15, 2, 803; 530/314, 328, 345, 402

[56] References Cited

U.S. PATENT DOCUMENTS

| | | | |
|---|---|---|---|
| 4,618,598 | 10/1986 | Conn et al. | 514/6 |
| 4,894,443 | 1/1990 | Greenfield et al. | 530/388 |

OTHER PUBLICATIONS

Carr, "The Effect of Anit–Inflammatory Drugs on Increased Vascular Permeability Induced by Chemical Mediators," The Journal of Pathology, vol. 108 (1), (1972) pp. 1–14.
Calixto et al, "Nonpeptide Bradykinin Antagonists", (1991), pp. 97–129 *The Journal of Pathology,* vol. 108 (1), pp. 1–14 (1972).

Cheronis et al, "Bradykinin antagonists: Synthesis and in vitro Activity of Bissuccinimidoalkane Peptide Dimers" Recent Progress on Kinins, (1992) pp. 551–558.

Whalley et al., 'Novel Peptide Heterodimers Withactions At BK2 And Either u Opioid, NK1 Or NK2 Receptors: In Vitro Studies', British Journal of Pharmacology, vol. 109, Suppl., 19P, Jul. 1993.

Vaverk et al., 'Suyccinyl Bis–Bradykinins: Potent Agonists with Exceptional Resistance to Enzymatic Degradation', Peptide: Struc. and Func., Proceedings of the 8th Amer. Pept. Symp., Pierce Chem. Co., Rockford, IL, pp. 381–384 1983.

Stewart et al., Bradykinin Chemistry: Agonists and Antagonist, Advances in Experimental Medicine and Biology, Plenum Press, NY, NY pp. 585–589 1983.

Calixto et al., 'Nonpeptide Bradykinin Antagonist', Bradykinin Antagonists: Basic and Clinical Research, Ronald Burch (Ed.), Marcel Dekker Inc., NY, NY, pp. 97–129 1991.

Kodama et al., 'Dimerization of neurokinin A and B COOH–terminal heptapeptide fragments enhanced the selectivity for tachykinin receptor subtypes', European Journal of Pharmacology, 151, pp. 317–320 1988.

*Primary Examiner*—Cecilia J. Tsang
*Assistant Examiner*—Anish Gupta
*Attorney, Agent, or Firm*—Cushman Darby & Cushman IP Group of Pillsbury Madison & Sutro LLP

[57] ABSTRACT

A bradykinin antagonist of the formula:

(BKAn)(X)(Y)

where BKAn is a bradykinin antagonist peptide; Y is a pharmacore; and X is a bridging link chemically joining the BKAn and Y components.

11 Claims, 9 Drawing Sheets

I. R = NH-CH$_2$-CH$_2$-S-CH$_2$-C$_6$H$_5$

III. R = NH$_2$

IV. R = NH-CO-CH$_2$-NH-COO-C(CH$_3$)$_3$

V. R = NH-CO-CH$_2$-NH-CO-CH$_2$-CH$_2$-S-CH$_2$-C$_6$H$_5$

VII. R' = NH-(CH$_2$)$_2$-S-CH$_2$-C$_6$H$_5$

VIII. R' = NH-(CH$_2$)$_2$-S  S-[CP-0126]

(CP-0494)

IX. R' = NH-(CH$_2$)$_2$-S  S-[CP-0347]

(CP-0499)

X. CP-0126 -BMH =

D-Arg-Arg-Pro-Hyp-Gly-Phe-Cys-D-Phe-Leu-Arg

XI. CP-0347 - BMH =

D-Arg-Arg-Pro-Hyp-Gly-Thi-Cys-D-Tic-Oic-Arg

BRADYKININ ANTAGONIST

RELATED APPLICATION

This is a continuation of application Ser. No. 08/296,185, filed Aug. 29, 1994, which is an CON of 07/974,000, filed Nov. 10, 1992, now abandoned which is a CIP of 07/859,582 filed Mar. 27, 1992 now abandoned and which is a CIP of 07/677,391 filed Apr. 1, 1991 now abandoned.

The present invention relates to pharmaceutically effective heterodimers comprising a bradykinin antagonist (BKAn) component covalently linked to another different pharmacophore component.

In the prior applications mentioned above, there are described bradykinin antagonist dimers of the type:

where BKAn represents a bradykinin antagonist peptide and X is a linking group which joins the two BKAn components at points intermediate to their ends. The BKAn substituents may be the same or different. However, also described are certain heterodimers involving the linkage of a BKAn peptide and another peptide of different receptor activity through the linking group X, e.g. an $NK_1$ or $NK_2$ antagonist peptide or a mu-opioid receptor agonist peptide. Such heterodimers are particularly useful where there is a close relationship between the activities of concern. Thus, it is known that in a number of pathophysiologically important processes, there is an intimate interaction of inflammatory and neurogenic mediators. This occurs, for example, in both pain secondary to tissue trauma (accidental and post-operative) as well as in asthma. In both situations, there is a complex interplay of tissue and plasma derived mediators (such as kinins acting at $BK_2$ receptors) and neuronally derived factors such as substance P ($NK_1$ receptors) and neurokinin A ($NK_2$ receptors). There are also locally acting neuronal receptors of the mu-opiate class that when stimulated can inhibit the release of the neurogenic peptides regardless of type (substances P, neurokinin A, neurokinin B, cholecystokinin, CGRP, etc.).

Given the interaction of these as well as other inflammatory and neurogenic mediators, no one agent is likely to be universally efficacious in ameliorating the symptoms attendant to the pathophysiology. The heterodimers described in the above-noted applications are directed towards addressing these problems with single agents possessing dual selectivity. Other advantages of such heterodimers will also be appreciated by those in the art.

BRIEF DESCRIPTION OF THE INVENTION

The present invention, in its broadest aspect, is concerned with heterodimers obtained by linking a BKAn peptide to another pharmacophore which is not a bradykinin antagonist, i.e. which may be either a peptide as described in the afore-mentioned applications Ser. No. 07/677,381 and Ser. No. 07/859,582, or a non-peptide, effective against a different, non-bradykinin component responsible, for example, for pain and/or the inflammatory process, or other problems related to or occurring in concert with the activity of the kinins. The resulting compounds are "dual action" compounds that are capable of interacting with two receptor populations or, alternatively, with a receptor and an enzyme. This is not intended to suggest that the single molecule will engage two receptors or a receptor and an enzyme simultaneously; only that the molecule is capable of interacting with either one of two receptor types or with a single class of receptors and/or an enzyme. The overall pharmacological effect of administering such a compound in an appropriate dose, however, is at least the summation of the two types of activities. The compounds can be designed to remain intact or they can be designed to be dissociated into two separate molecules each retaining its own identifiable activity.

The heterodimers of the invention can be structurally represented as follows:

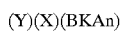

where BKAn is a bradykinin antagonist peptide; X is a linking group and Y is a peptide or non-peptide pharmacophore which is not a bradykinin antagonist and demonstrates activity towards a different receptor or enzyme than the BKAn component, preferably one related to pain or the inflammatory process.

The present heterodimers offer the possibility of providing a wider spectrum of treatment for pain and inflammation. It is a generally held opinion that in inflammatory states, regardless of severity, the likelihood that a single agent or mediator is completely responsible for all of the clinical manifestations of the syndrome being addressed is extraordinarily small. A corollary to this is that, given the role of bradykinin in inflammatory pathophysiology, any combination therapy used in the treatment of inflammatory disorders should include bradykinin antagonism as part of its overall profile of action. Broad spectrum and potent non-specific therapies (such as the use of steroids in asthma) while perhaps efficacious, carry with them the burdens of undesired and potentially serious side effects and toxicities.

In many cases, two discrete mediators are known to act synergistically and to account for an overwhelming proportion of the clinically important manifestations of the disease being treated. Such is the case, for example, with substance-P acting at $NK_1$ receptors and bradykinin acting at $BK_2$ receptors in the contexts of asthma and post-traumatic or post-operative pain. Similarly, neutrophil elastase as one of the more important down stream effectors of inflammation and bradykinin as one of the more important initiating and sustaining inflammatory mediators also can be viewed as being synergistic in their actions.

The concept of providing homodimers of pharmaceutically active materials to improve such characteristics as metabolic stability, selectivity and receptor binding has previously been described for other systems. This prior work has included the dimerization of peptide agonists and antagonists in order to increase potency and/or duration of action. See, Caporale et al, *Proc. 10th American Peptide Symp.*, Pierce Chemical Co., Rockford, Ill. 449–451 (1988) and Rosenblatt et al, European Patent Application No. EP 293130A2. Thus, dimerization of peptide agonists has been disclosed for enkephalins/endorphins (Shimohigashi, Y., et al, *BBRC,* 146, 1109–1115, 1987); substance P (Higuchi, Y., et al, *E.J.P.,* 160, 413–416, 1989); bradykinin (Vavrek, R. and Stewart, J., *J. Proc. 8th Amer. Pept. Symp.*, 381–384, 1983); neurokinin A & B, (Kodama, H., et al, *E.J.P.,* 151, 317–320, 1988); insulin (Roth, R. A., et al, *FEBS,* 170, 360–364, 1984) and atrial natriuretic peptide (Chino, N., et al, *BBRC,* 141, 665–672, 1986). Dimerization of antagonists has been shown for parathyroid hormone (Caproale, L. H., et al, *Proc. 10th Amer. Pept. Symp.,* 449–451, 1987)). However, the literature has not disclosed heterodimers comprised of a bradykinin antagonist and a different pharmacophore as contemplated herein.

DETAILED DESCRIPTION OF THE INVENTION

Figure 1A:
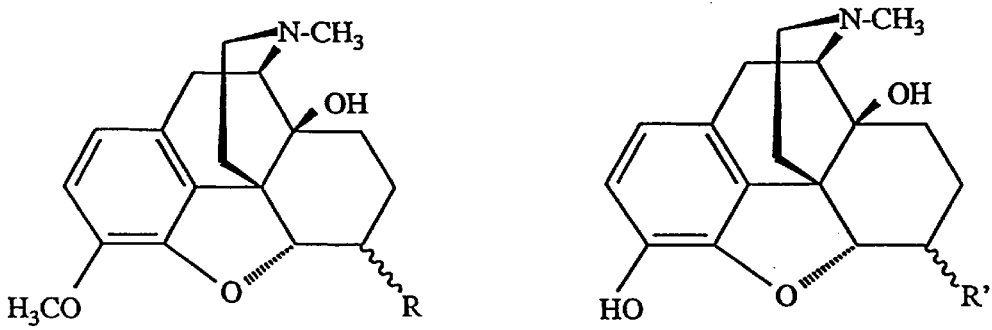
FIGS. 1A and 1B show structural details of some of the compounds or the present invention and some intermediates used in the preparation thereof.
Figure 1A:
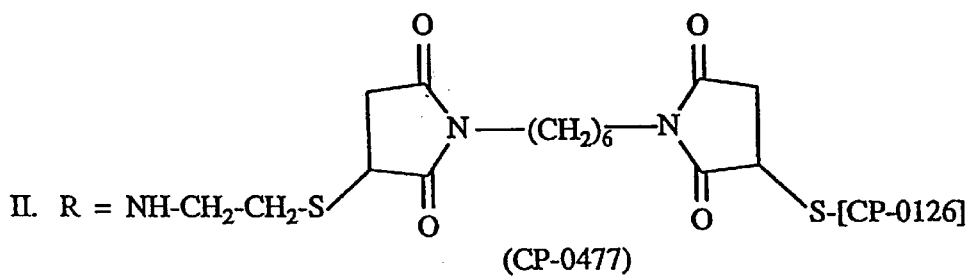
Figure 1A:
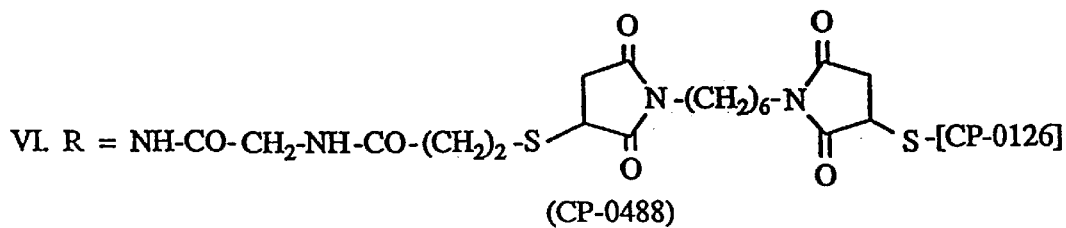
Figure 1B:
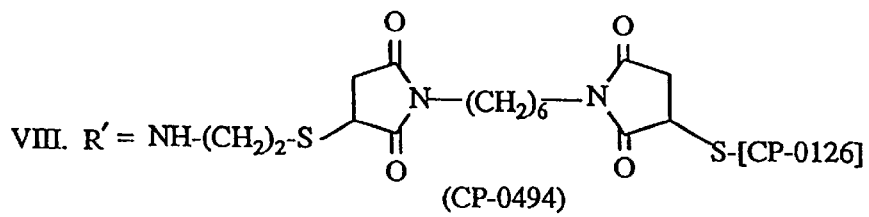
Figure 1B:
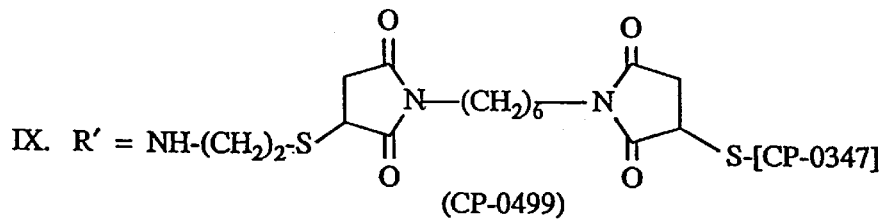
Figure 1B:
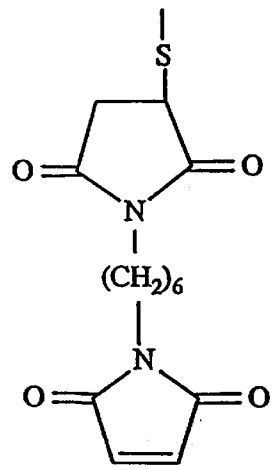
Figure 1B:
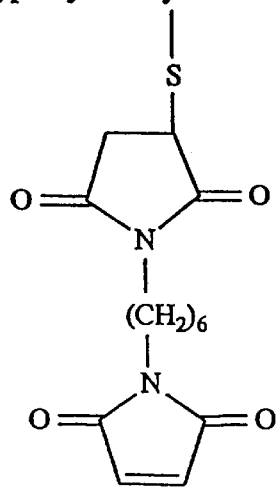

Numerous bradykinin antagonist peptides are known in the art and any of these may be used for present purposes to provide the BKAn substituent of the present dimers. One of the more potent bradykinin antagonists in vitro is the peptide having the formula:

$$D\text{-}ARG^0\text{-}Arg^1\text{-}Pro^2\text{-}Hyp^3\text{-}Gly^4\text{-}Phe^5\text{-}Ser^6\text{-}D\text{-}Phe^7\text{-}Leu^8\text{-}Arg^9$$

See Regoli et al, *Trends in Pharmacological Science,* 11:156–161 (1990). This peptide is referred to herein for convenience as CP-0088.

While CP-0088 is a convenient BKAn to use, those in the art will appreciate that other available or known bradykinin antagonist peptides can also be used for present purposes. A wide variety of such bradykinin antagonist peptides have been disclosed in the recent patent literature and any of these can be used for present purposes. See, for example, EP-A-0334244 (Procter and Gamble) which discloses nona- and larger bradykinin antagonist peptides in which certain amino acid residues are modified. EP-A-0370453 (Hoechst) and WO 89/01780 and WO 89/01781 (Stewart et al) also describe bradykinin antagonist peptides. None of these patent publications appears to show dimers as contemplated herein. However, as noted, the peptides of these publications can be used in the practice of the present invention.

Any linking group X may be used for present purposes to chemically or covalently link together the BKAn and Y components provided this does not interfere with the activity of the components BKAn and Y. The linking group may be inorganic (e.g. —S—) or organic and may be selected so as to hydrolyze or otherwise dissociate in order to liberate the two active components BKAn and Y in vivo. Alternatively, the linking group may be such that the heterodimer remains intact when used.

Conveniently the linking group X can include an —S— atom derived by reacting a sulfhydryl group on the BKAn peptide chain with the other pharmacophore component. This can be accomplished by reaction involving a cysteine (Cys) sulfhydryl group within the peptide chain, i.e. intermediate the ends of the peptide. This may require initially modifying the starting BKAn peptide so that it includes a Cys group in the appropriate position in the peptide chain. For example, CP-0088 may be modified by replacing the Ser in the 6-position with Cys (such modified CP-0088 being called CP-0126 hereinafter) to provide for convenient linking to the other pharmacophore through the Cys sulfhydryl.

CP-0126 can be structurally illustrated as follows:

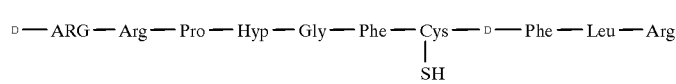

In abbreviated fashion, the formula may be stated as:

DR-R-P-J-G-F-C-DF-L-R

Using Cys as the position of attachment, the linking group X then includes the —S— of the cysteine sulfhydryl. This may be the entire linking group X (as in a disulfide based dimer) or only a part thereof. Thus, for example, the linking group may comprise a bissuccinimidoalkane such as bis-succinimidohexane joined at its end to the BKAn and Y components. These and other linking groups are disclosed in the related applications referred to earlier herein and any of these may be used for present purposes. Other linking groups X, some of which do not require or contained an —S— atom, can be derived from the six families of compounds listed below which can be generically categorized as amino acid analog linkers or maleimide-based linkers. These linkers are included as examples only and are not intended to be totally inclusive of all potential linking moieties:

CLASS I (Amino Acid Analogs)

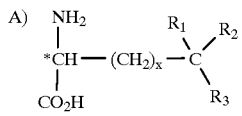

\* - "D" or "L" Configuration
$R_1$ & $R_2$ = ——H, ——$CH_3$, ——$CH_2$—$CH_3$
or --$R_1/R_2$-- = CYCLO ALKYL
$R_3$ = ——OH, ——$CO_2H$, or ——$NH_2$
x = 1 - 12
y = 1 - 4

B) 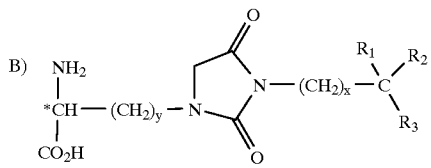

C) 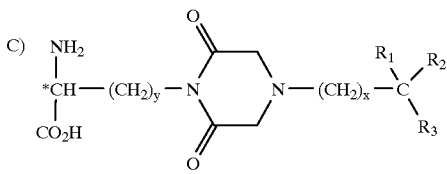

D) 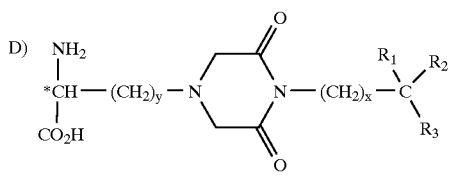

E) 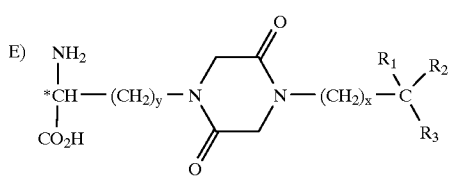

CLASS II (Maleimide Based Linkers)

F) 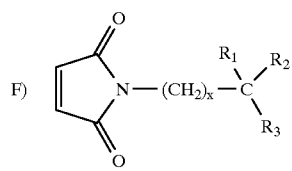

The amino acid analog linkers (Class I) can be directly incorporated into the peptide chain of the BKAn and then used to form esterase stable or labile heterodimers with the geminal pharmacophore (component Y). Alternatively, the maleimide based linker can be reacted with the desired pharmacophore and then conjugated to a sulfhydryl containing peptide. Finally, linkers from any of these families of compounds which contain —$CO_2H$ as the $R_3$ moiety can be reacted with another linker from these classes of compounds to form esterase labile ($R_3$=—OH containing linkers) or esterase stable ($R_3$=—$NH_2$ containing linkers) which can then be used to form the desired peptide/non-peptide heterodimer. $R_1$ and $R_2$ can be varied so as to provide for completely unhindered or significantly hindered access to the carbonyl carbon of an ester based linking element so that the rate of in vivo hydrolysis of said ester can be controlled as desired.

Certain of the linker-modified BKAns or pharmacophores used herein to prepare the dimers of the invention are themselves novel and constitute a further aspect of the invention.

The component Y of the present heterodimers may be any peptide or non-peptide pharmacophore, other than a bradykinin antagonist, which demonstrates activity towards a different (non-bradykinin) component related to pain and/or the inflammatory process so as to provide dual action compounds that are capable of interacting independently with two different receptor populations or a receptor and an enzyme. Thus, for example, the component Y may be a non-peptide mu-opioid receptor agonist, e.g. morphine or one of its derivatives such as oxycodone or oxymorphone.

Indomethacin is a useful choice for the Y component when cyclooxygenase inhibition (COI) is desired. However, any of the other conventional non-steroidal anti-inflammatory agents, such as aspirin, ibuprofen, naproxyn or the like can be used. In this case, the BKAn/COI heterodimer may need to be hydrolyzed in order to obtain in vivo COI activity as cyclooxygenase is generally considered to be an intra-cellular enzyme.

Where neutrophil elastase inhibition is required, this may be an active ester, e.g. one of those described in U.S. applications Ser. No. 07/528,967, filed May 22, 1990; Ser. No. 07/692,322, filed May 2, 1991 or Ser. No. 07/841,608, filed Feb. 25, 1992, the contents of which are incorporated herein by reference. The esters described in said applications are 2-phenyl-alkanoate esters. There may also be used a heteroaryl alkanoate esterase inhibitor as described in Ser. No. 07/866,301, filed Apr. 13, 1990 and Ser. No. 07/610,207, filed Nov. 7, 1990, the contents of which are included herein by reference. A preferred neutrophil elastase inhibitor for use herein as component Y is identified below as CE-1218. This is believed to be a new compound and constitutes a further feature of the present invention.

Other types of elastase inhibitors which may also be used as component Y, include fluoromethyl ketones, phosphonates, benzoxazoles, beta-lactams, etc.

As noted earlier, component Y may comprise a peptide or non-peptide inhibitor having a desired activity other than bradykinin antagonist activity. However, the Y component is preferably selected to provide activity against receptors or enzymes which have a common or close relationship to the activity of bradykinin, e.g. the treatment of pain or inflammation. The rationale for using combinations of a BKAn with a mu-opioid receptor agonist, neutrophil elastase inhibitor, cyclooxygenase inhibitor or $NK_1$ or $NK_2$ receptor antagonist in various conditions is discussed below for purposes of illustration.

BKAn/mu-opioid Receptor Agonists

C-Fiber afferents are known to mediate both the sensation of pain as well as the neurogenic component of inflammation. These afferent neurons release a variety of neuropeptides in response to specific and non-specific stimuli in both the central nervous system (CNS) as well as in the peripherally innervated tissues. Some of these neuropeptides include: substance-P, neurokinin A, neurokinin B, calcitonin gene related peptide (CGRP), cholecystokinin (CCK), vasoactive intestinal polypeptide (VIP), and neuropeptide Y, among other neurotransmitters. To add to this complexity, different C-fibers appear to contain different amounts and/or ratios of these neuropeptides depending on the tissue innervated. All of these peptides have been shown to play contributory roles in the various neurogenic processes that have been implicated in numerous diseases and clinical syndromes. In fact, specific antagonists to these peptides are being developed as potential therapeutics by a variety of pharmaceutical companies and independent research laboratories.

One apparently common feature among this otherwise diverse group of neurons is that they all have mu-opioid receptors that modulate the release of these neuropeptides. Both the endogenous enkephalins as well as other exogenously administered small molecular weight compounds such as morphine, oxymorphone, fentanyl and their derivatives will inhibit the release of the neuropeptides from peripheral C-fibers by acting as mu-opioid receptor agonists locally (at terminal mu-opioid receptors in the periphery) and in the CNS. This inhibition is independent of both the constellation of peptides contained in the specific C-fiber as well as the stimulus causing their release.

As a result, one important class of compounds considered to have a particularly good profile of activities for the treatment of conditions that are produced by combined humoral and neurogenic processes are BKAn/mu-opioid receptor agonist heterodimers. These compounds would be expected to attenuate or block both the humoral component of the inflammatory process as represented by the kinins as well as the neurogenic aspects of inflammation produced by the release of the neuropeptides. In addition, one of the limiting aspects of the use of existing mu opioid agonists is their propensity to produce sedation, confusion, and a depressed respiratory drive, not to mention their potential for the development of addiction and/or tolerance in the patients being treated with these agents. These undesirable aspects of mu-opioid receptor agonists are due to their ability to easily penetrate the CNS. BKAn/mu-opoid receptor agonist heterodimers, however, should not penetrate the CNS due to the highly cationic nature of the BKAn. Consequently, mu-opioid receptor agonist activity should be limited to the periphery and should result in a substantially reduced side effect/toxicity profile for these types of compounds.

BKAn/Neutrophil Elastase Inhibitor (NEI)

As previously mentioned the control of both systemic and local inflammatory responses may require interventions in more than one inflammatory pathway. In particular, the ability to block the activity of a primary mediator responsible for the initiation and maintenance of the inflammatory process (such as bradykinin) and a primary final pathway effector responsible for actual tissue degradation and injury (such as neutrophil elastase) may be a key to "single drug therapy" of sepsis or other severe inflammatory conditions requiring parenteral therapy or for the treatment of inflammatory dermatologic or dental/periodontal conditions.

Heterodimers containing combined BKAn/NEI activities can be designed to remain intact or to be dissociable as both targets (bradykinin receptors and neutrophil elastase) are extracellular in nature. However, should dissociation of the two active pharmacophores be desired, linking moieties tethering the two active components of the heterodimer can be designed to be hydrolyzed by, for example, plasma hydrolases. These types of dissociable or hydrolyzable heterodimers are discussed herein.

BKAn/Cyclooxygenase Inhibitor (COI)

A large proportion of the biological activity of bradykinin is interwoven with the generation of prostaglandins. For example, much of the hyperalgesia associated with inflammatory pain appears to be dependent on the generation of certain prostaglandins both by the injured tissues and by the C-fibers themselves. In the latter case, bradykinin and substance-P appear to be the primary stimuli for these "second messengers". The local generation of prostaglandins by the injured tissues is bradykinin independent. This interaction of peptide pro-inflammatory mediators and prostaglandins occurs in other settings as well and can also be considered a target for dual action compounds. Heterodimers containing combined BKAn/COI activities may need to undergo in vivo dissociation of the respective pharmacophores as cyclooxygenase is an intracellular enzyme and functional bradykinin receptors are limited to the external plasma membrane.

BKAn/NK$_1$-Receptor Antagonist (NK1An)

Bradykinin and substance-P are known to act synergistically in the initiation and maintenance of the inflammatory and neurogenic components of both asthma and a variety of painful conditions. In both of these situations, bradykinin is one of the more potent, if not the most potent, agents capable of stimulating C-fiber sensory afferents that mediate peripheral pain and/or the sensation of cough and dyspnea in asthma. These neurons, regardless of the primary stimulus, will release substance-P which amplifies and augments the activity of bradykinin and other stimuli at the sensory nerve endings where these stimuli are acting. This "one/two punch" of initial stimulus followed by local amplification is well documented and has significant implications for the success or failure of any single intervention. By targeting both components of these processes with a single compound, it is possible to provide a dually-specific agent which is superior than mono-specific agents used alone and both easier and cheaper to use than combination therapies.

BKAn/NK$_2$ Antagonist (NK2An)

Bradykinin's ability to produce acute bronchial smooth muscle constriction is at least partially dependent on the release of neurokinin A by the same C-fibers that release substance-P. Neurokinin A exerts its effect via NK$_2$ receptors on the bronchial smooth muscle. However, more than just bradykinin can release neurokinin A from these neurons and, as a result, a dually-specific antagonist with combined BK$_2$/NK$_2$ antagonist activity should provide better overall amelioration of bronchoconstriction in the asthmatic patient than any other single agent.

The heterodimers of the invention may be prepared in generally the same manner as described in the above-mentioned Ser. No. 07/859,582 and Ser. No. 07/677,391. Normally this involves adding the linking group X to the BKAn component at an appropriate position along the peptide chain followed by joining the non-peptide pharmacophore to the BKAn through the linking group. Alternatively, the linking group may be added to the non-peptide pharmacophore and the BKAn thereafter joined to the linker-modified pharmacophore. Representative procedures are described below although it will be recognized that various modifications may be used.

The invention is illustrated but not limited by the following examples:

EXAMPLES 1–4 (BKAn/MU-OPIOID AGONIST)

Four different peptide/opiate heterodimers (designated CP-0477, CP-0488, CP-0494 and CP-0499) were made in order to illustrate the invention. Three of these compounds were made using CP-0126 (DR-R-P-J-G-F-C-DF-L-R) and the fourth used CP-0347 (DR-R-P-J-G-Thi-C-DTic-Oic-R). Similarly, two different opiates (oxycodone and oxymorphone) and two different linker chemistries were used to provide the respective heterodimers as follows:

| Example | Compound # | Peptide | Opiate |
| --- | --- | --- | --- |
| 1 | CP-0477 | CP-0126 | Oxycodone |
| 2 | CP-0488 | CP-0126 | Oxycodone |
| 3 | CP-0494 | CP-0126 | Oxymorphone |
| 4 | CP-0499 | CP-0347 | Oxymorphone |

The heterodimers CP-0477, CP-0488, CP-0494 and CP-0499 were prepared as detailed hereinafter with reference to the accompanying FIG. 1:

Preparation of Compound I

Oxycodone hydrochloride (0.182 g, 0.52 mmol), acetic acid (0.475 ml, 8.3 mmol), S-benzyl cysteamine (0.174 g, 1.04 mmol) and methanol (5 ml) were combined and stirred at room temperature for an hour. Sodium cyanoborohydride (95%, 0.033 g, 0.52 mmol) was added, and the reaction stirred at room temperature for 24 h. The mixture was concentrated in vacuo. The resulting oil was dissolved in ethyl acetate and the ethyl acetate fraction was washed with saturated sodium bicarbonate solution, dried over magnesium sulfate and evaporated in vacuo. The crude material was chromatographed on a silica column and eluted with EtOAc, EtOAc-MeOH (9:1, v/v) and EtOAcMeOH-Et$_3$N (9:1:0.2, v/v/v) successively Compound I was isolated as an oil in 25.0% (59.0 mg) yield.

Preparation of Compound II (CP-0477)

I (0.059 g, 0.127 mmol) was dissolved in 2 mL dry tetrahydrofuran, and was transferred to a oven dried three-necked 100 ml flask. The flask was fitted with a dewar condenser, a nitrogen source and an ammonia inlet. Approximately 10 ml of ammonia was condensed into the flask maintained at −78 C. Small pieces of sodium were added until the intense blue color was maintained and then quenched after 40 seconds with solid ammonium chloride. The reaction mixture was allowed to warm to room temperature and the ammonia boiled off through a bubbler, methanol (25 ml×3) was added and evaporated in vacuo. The thiol isolated was dissolved in a minimum quantity of DMF (N, N-dimethyl formamide, 2 ml). Compound X (approximately 0.3 equiv) was dissolved in tris buffer (0.5 M, 4.0 ml) and added to the DMF solution and then stirred for 17 h. The crude mixture was purified on a reverse phase Vydac C-18 HPLC column using the gradient 15–40% CH$_3$CN in water, 0.1% constant TFA, over 20 minutes. Retention time was 16.0 minutes. 26.4 mg of II was isolated as a white powder on lyophillization.

Analysis

The mass spectra was run on a Finnigan Lasermat Mass Analyzer.

calulated molecular weight—1916
observed molecular weight—1918

Amino Acid Analysis

Gly 1.02 (1), Arg 3.14 (3), Pro 1.01 (1), Leu 0.97 (1), Phe 1.92 (2) and Hyp 0.94 (1).

Preparation of Compound III

To the mixture of oxycodone hydrochloride (1.0 g, 2.84 mmol) and ammonium acetate (2.2 g, 28.4 mmol) dissolved in methanol (10.0 ml) was added a methanolic (4.0 ml) solution of NaCNBH$_3$ (0 18 g, 2.84 mmol). The resulting solution was adjusted to pH 7.0 with concentrated hydrochloric acid, stirred for 17 h, and acidified to pH 1.0 with concentrated hydrochloric acid. The solvent was removed in vacuo and the remaining material was dissolved in water. The aqueous layer was extracted with chloroform, adjusted to pH 9.0 with 10% sodium carbonate solution, saturated with NaCl and extracted with chloroform. The chloroform layer was dried over magnesium sulfate and evaporated in vacuo. The crude oil was purified by silica gel chromatography and eluted with EtOAc, EtOAc-MeOH (9:1, v/v), EtOAc-MeOH-Et$_3$N (9:1:0.3, v/v/v) successively. Compound III was isolated as an oil in 47 0% (0.42 g) yield.

Preparation of Compound IV

BOC-Glycine (0.16 g, 0.91 mmol), HOBt (0.125 g, 0.91 mmol) and 1-(3-dimethylaminopropyl)-3-ethylcarbodiimide hydrochloride (EDC) ( 98 0%, 0.18 g, 0.91 mmol) were dissolved in DMF (2.0 ml) and stirred at 0° C. for an hour. The amine III (0.24 g, 0.76 mmol) dissolved in DMF (3.0 ml) was added to the reaction mixture, the reaction mixture was warmed to room temperature and stirred for 17 h. DMF was removed in vacuo and the resulting material was dissolved in ethyl acetate. The ethyl acetate layer was washed with saturated sodium bicarbonate solution, brine and dried over magnesium sulfate. The organic layer was evaporated in vacuo and the crude mixture was flash chromatograhed on a silica gel column and eluted with EtOAc-MeOH-Et$_3$N (9.5:0.5:0.3, v/v/v). Compound IV was isolated as an oil in 82.0% (0.29 g) yield.

Preparation of Compound V

The BOC protecting group was removed off the compound IV with TFA (5.0 ml) in methylene chloride (5.0 ml). Methylene chloride was removed in vacuo and the residue was stripped with methylene chloride (20 ml×3) and then with triethyl amine (3 ml×3). 3-S-benzyl mercapto propionic acid (0.15 g, 0.75 mmol), EDC (0.15 g, 0.75 mmol), HOBt (0.103 g, 0.75 mmol) and Et3N (0.35 ml, 2.48 mmol)were dissolved in DMF (5.0 ml) and stirred at 0° C. for an hour. The solution of the amine (0.23 g, 0.62 mmol) in DMF (3.0 ml) was added to the reaction mixture. The reaction mixture was warmed to room temperature and stirred for 17 h. DMF was evaporated in vacuo and the residue was dissolved in EtOAc. The EtOAc layer was washed with 10% Na$_2$CO$_3$, brine, dried (over MgSO$_4$) and evaporated in vacuo. The crude material was purified on a flash silica gel column and eluted with EtOAc-MeOH-Et$_3$N (9:1:0.3, v/v/v). Compound V was isolated as an oil in 60.0% (0.205 g) yield.

Preparation of Compound VI (CP-0488)

32.0 mg (0.057 mmol) of V was deprotected using the procedure described for II and the thiol isolated was reacted with compound X (0.073 g, 0.048 mmol) in tris buffer. The crude mixture was purified using the procedure for II. Retention time of the product was 16.82 minutes. 9.5 mg (10%) of VI was obtained as a white powder on lyophillization.

Mass Spectral Data
calulated molecular weight 2,002
observed molecular weight 2,004
Amino Acid Analysis
Gly 1.76 (2), Arg 3.19 (3), Pro 1.06 (1), Leu 0.99 (1), Phe 2.06 (2), Hyp 0.95 (1).

Preparation of Compound VII

Oxymorphone hydrochloride (0.56 g, 1.66 mmol), S-benzyl cysteamine (0.69 g, 4.15 mmol), acetic acid (1.52 ml, 26.5 mmol) and sodium cyanoborohydride (0.11 g, 1.66 mmol) were used according to the procedure for I. The composition of the third eluant, EtOAc-MeOH-Et$_3$N, used in the purification of the crude mixture was 9:1:0.3, v/v/v. On purification, 0.213 g of compound VII (29.0%) was isolated as an oil.

Preparation of Compound VIII (CP-0494)

VII (0.063 g, 0.14 mmol) was deprotected following the procedure for II. The thiol was then treated with X (0.335 g, 0.152 mmol) in tris buffer. The crude mixture was purified on a reverse phase Vydac C-18 HPLC column using the gradient 15–70% CH$_3$CN in water, 0.1% constant TFA over 35 minutes. VIII had a retention time of 15.0 minutes. 119.0 mg (45.0%) of VII was isolated as a white powder on lyophillization.

Mass Spectral Data
calculated molecular weight 1902
observed molecular weight 1904
Amino Acid Analysis
Gly 0.81 (1), Arg 3.12 (3), Pro 1.07 (1), Leu 0.99 (1), Phe 2.04 (2), Hyp 0.98 (1).

Preparation of Compound IX (CP-0499)

VII (0.009 g, 0.02 mmol) was deprotected following the procedure for II and the thiol was then reacted with XI (0.026 g, 0.016 mmol) in tris buffer. Crude mixture was purified on a Vydac C-18 reverse phase HPLC using the gradient 15–70% CH$_3$CN in water, 0.1% constant TFA, flow rate of 8.0 ml/min over 40 minutes. Retention time of IX was 14.22 minutes. IX (6.4 mg, 20.0%) was isolated as white powder on lyophillization.

Mass Spectral Data
Calculatedmolecularweight 1957
Observed molecular weight 1958

IN VITRO TESTING

The BKAn/mu-opioid receptor agonist heterodimers were evaluated in vitro using the rat uterus (BK$_2$-receptor activity) and the electrically stimulated guinea pig ileum (mu-opiate receptor activity) assays. These assays are well known in the art. The results obtained are shown in Table I:

TABLE I

| Compound | pA$_2$—Rat Uterus | IC$_{50}$ Guinea Pig Ileum (nmolar) |
| --- | --- | --- |
| CP-0126 | 7.1 | inactive |
| CP-0347 | 9.5 | inactive |
| oxycodone | inactive | inactive |
| oxymorphone | inactive | 21.7 |
| CP-0477 | 7.9 | inactive |
| CP-0488 | 8.2 | inactive |
| CP-0494 | 8.4 | 24.0 |
| CP-0499 | 8.9 | 17.0 |

It should be noted that neither oxycodone nor the heterodimers derived from oxycodone (CP-0477 and CP-0488) showed any activity in the in vitro guinea pig ileum assay of mu-opiate receptor agonist activity. This is probably due to the fact that for complete activity, oxycodone apparently needs to be demethylated in vivo. As a result, oxycodone and oxycodone-based compounds would not be expected to show activity in an assay wherein the appropriate demethylating enzymes were missing.

More important, however, are the data regarding the activity of the BKAn component of these heterodimers on the rat uterus and the data regarding the activity of the oxymorphone containing compounds. As can be seen from the data outlined in Table I, full BKAn activity was retained in all of these heterodimers and in those compounds utilizing oxymorphone as the opiate, full mu-opiate receptor agonist activity was also retained. From these data, it is evident that BKAn/mu-opioid receptor agonist heterodimers can interact with their respective receptor populations in in vitro systems.

IN VIVO TESTING

Figure 2A:
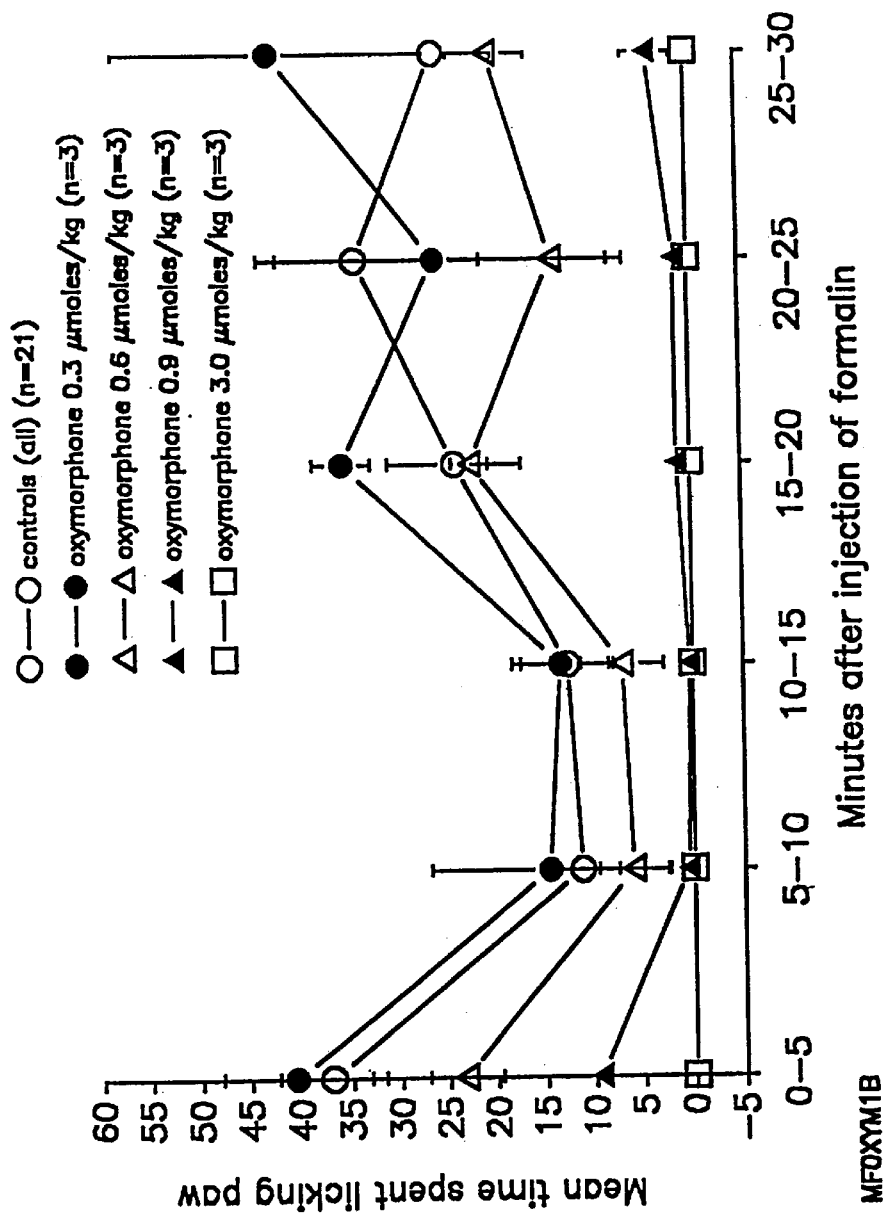
FIGS. 2A and 2B show the results obtained with oxymorphone in the mouse formalin test.
Figure 2B:
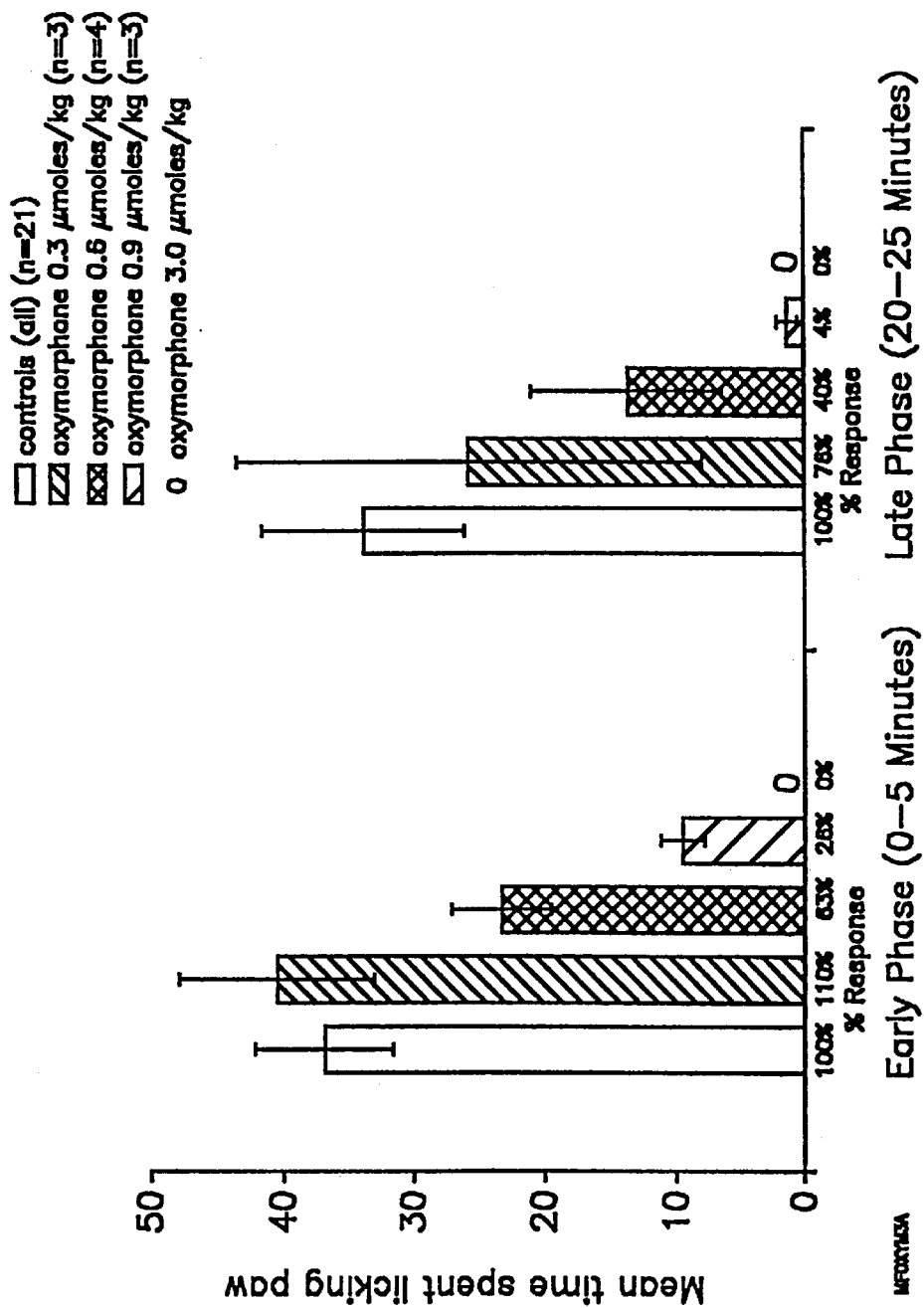
Figure 3A:
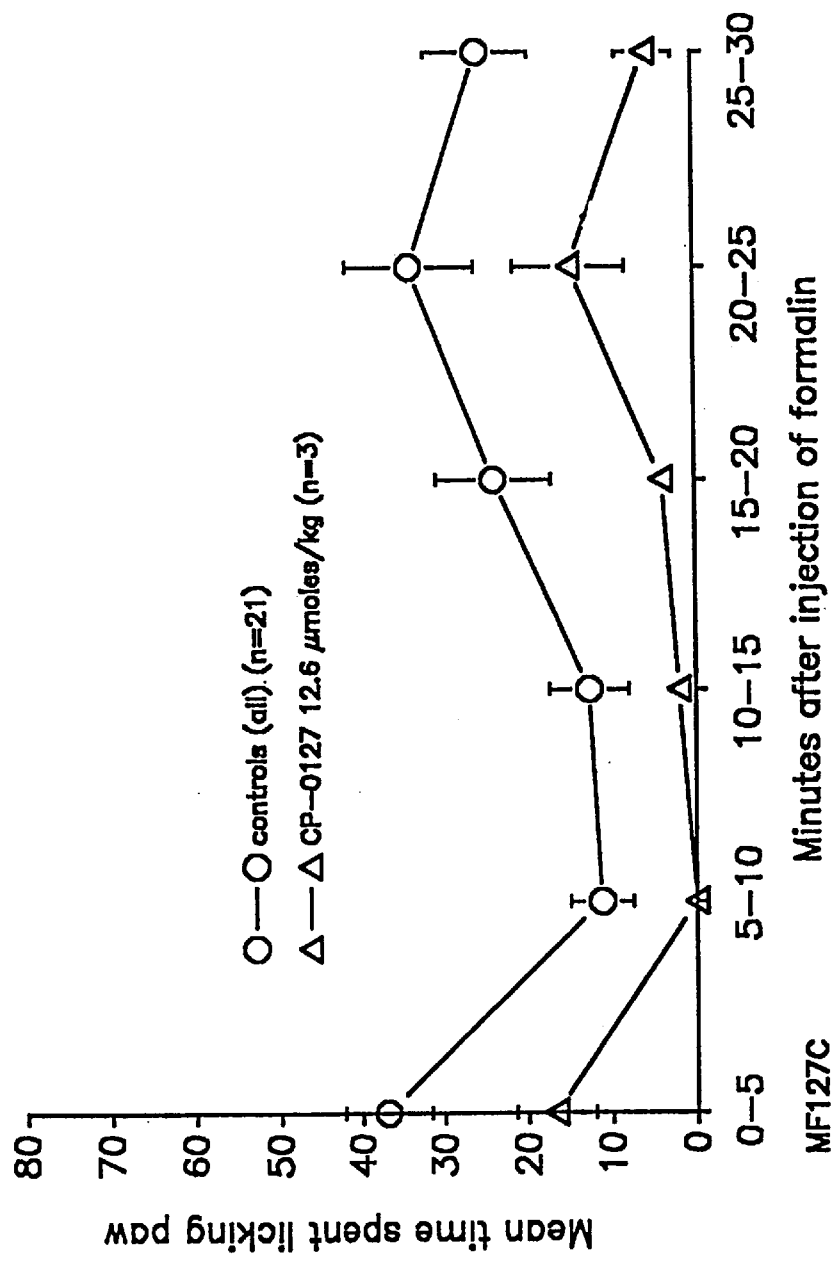
FIGS. 3A and 3B show the results obtained with compound CP-0127 in the mouse formalin test.
Figure 3B:
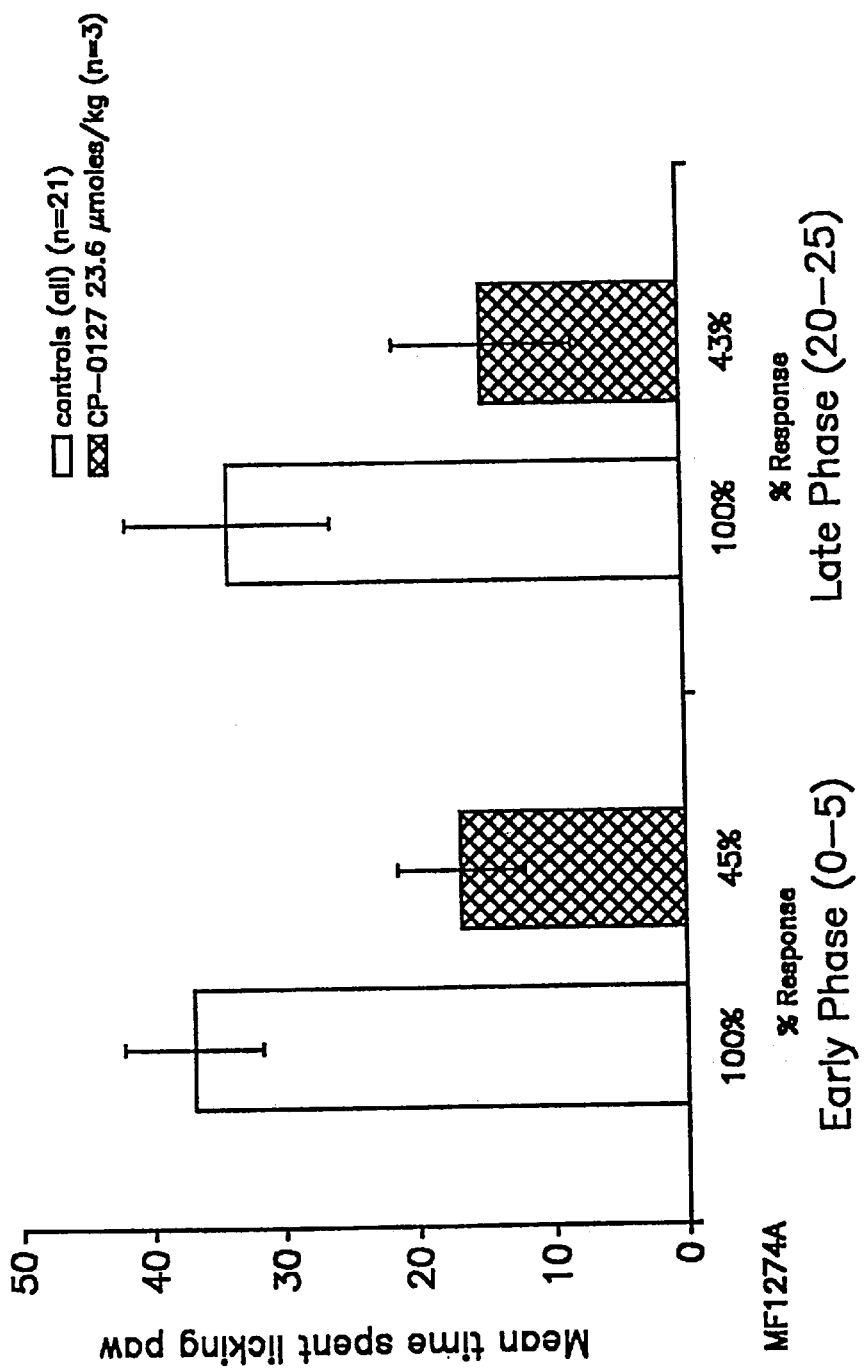
Figure 4A:
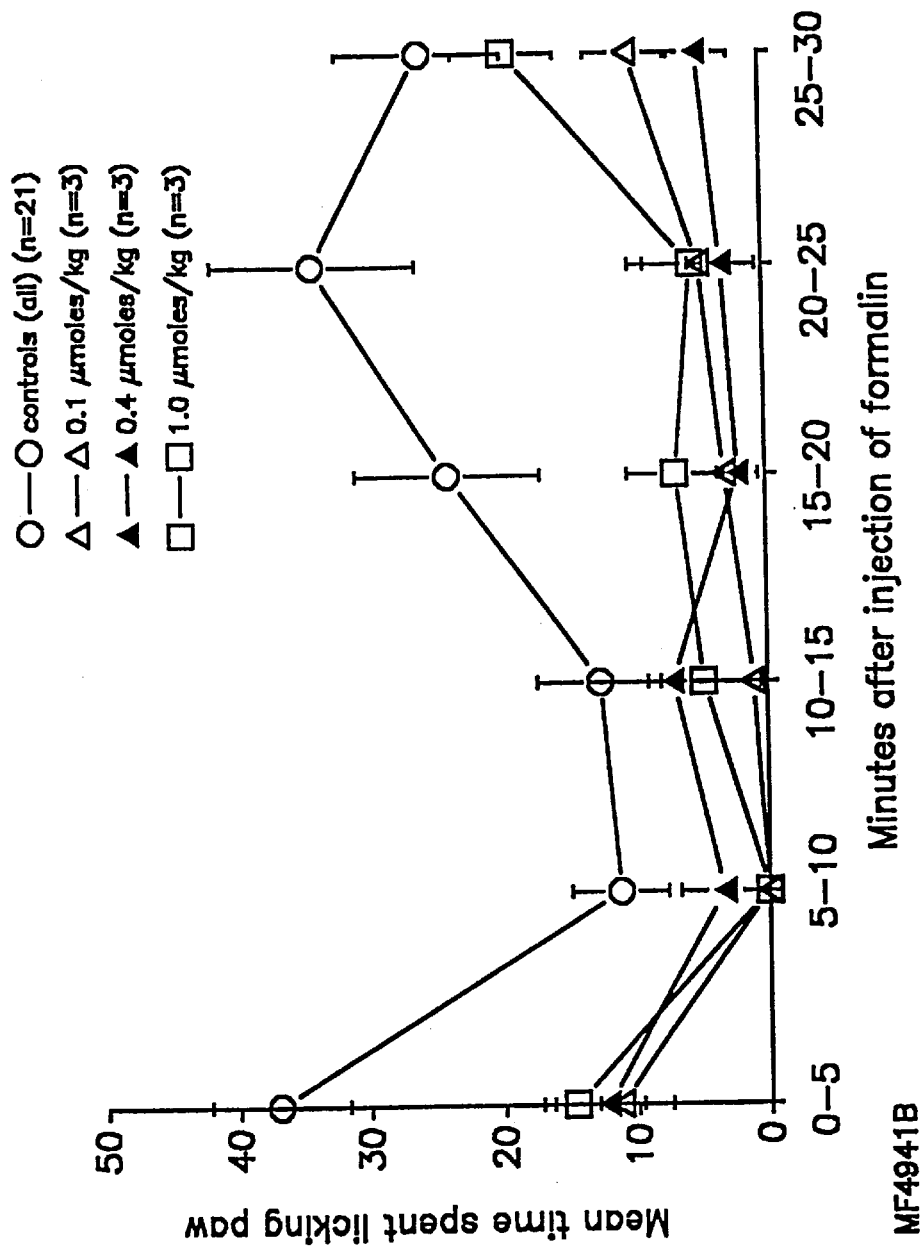
FIGS. 4A and 4B show the results obtained with compound CP-0494 in the mouse formalin test.
Figure 4B:
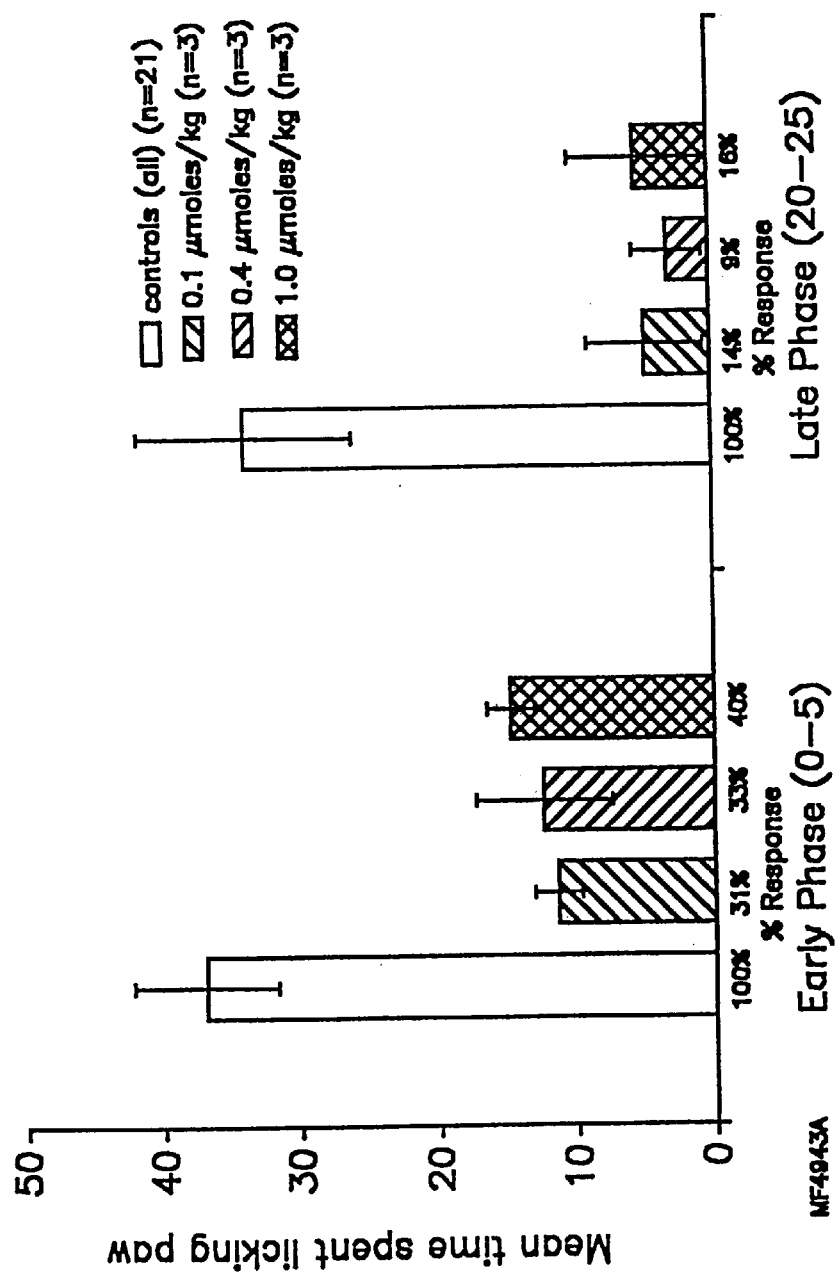

In order to test the activity of these compounds in vivo, a model of inflammatory and neurogenic pain was used. This model measures the behavioral responses of mice injected in the hind limb foot pad with 50 ul of formalin. The data from these studies are summarized in FIGS. 2, 3 and 4. Control mice (open circles) show a characteristic bi-phasic response to the injected formalin wherein there is a short lasting initial response followed by a quiescent period which is then followed by a sustained period of hind limb licking. The licking behavior is interpreted to mean that the limb is irritated and painful. The greater the time spent licking, the more painful the stimulus.

Oxymorphone (FIG. 2A and B) reduces both phases of the licking behavior but with significant behavioral obtundation resulting in catalepsy and frank respiratory depression at the highest doses (0.9 and 3.0 umoles/kg). The bradykinin antagonist CP-0127 (a potent $BK_2$ selective antagonist—FIGS. 3A and B) will reduce the time spent licking in both phases of the formalin test but at doses that are substantially greater than would be practical in a clinical setting. CP-0494 (FIGS. 4A and B), however, not only blocks both phases of the pain response, but does so at doses substantially lower (0.1 umoles/kg) than for either oxymorphone (0.9 umoles/kg) or CP-0127 (12.6 umoles/kg) alone and, of equal or greater importance, with no observable narcotic effects over several hours. These data indicate that BKAn/mu-opioid receptor agonist heterodimers are pharmacologically qualitatively superior to either of the parent pharmacophores as would be expected from the theoretical considerations outlined above.

One skilled in the art will appreciate that the compounds described are representative of a wide variety of compounds in which each of the components of the heterodimer (BKAn, linker and/or mu-opioid receptor agonist) can be varied to produce the optimal effect desired.

EXAMPLE 5 (BKAn/NEI)

A BKAn/NEI type of compound (CP-0502) of the structure shown in Synthetic Scheme 3, was synthesized to illustrate that this class of compounds can be used as a potent topical and/or systemic anti-inflammatory agent. This compound is derived from CP-0126 and the prototype elastase inhibitor, CE-1218 (see Compound (6), Synthetic Scheme 1 below).

SYNTHETIC SCHEME 1

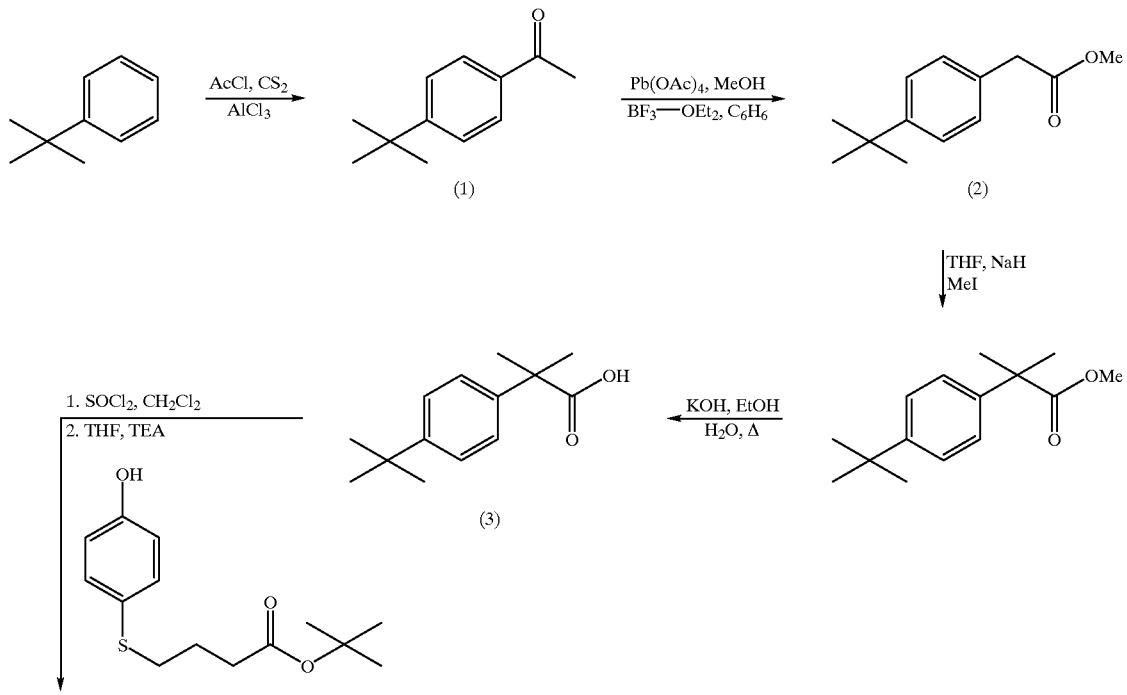

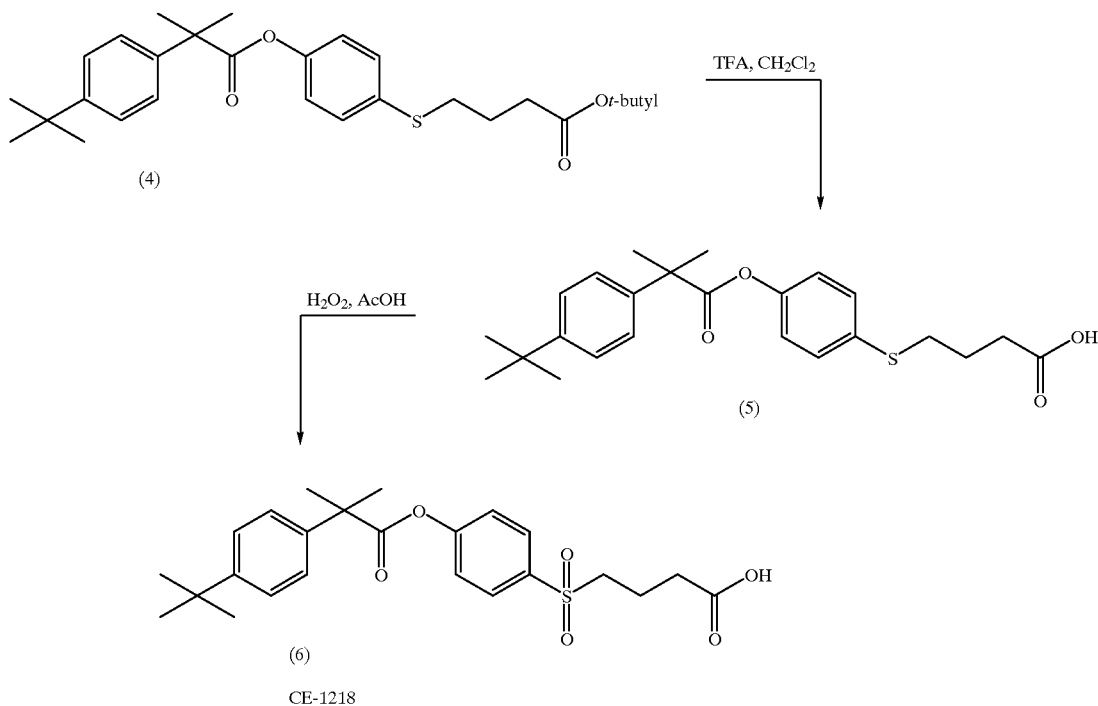

(CE-1218)

The linking element used in this heterodimer was chose so as to allow for unhindered hydrolysis of the joining ester bond by serum esterases. Those skilled in the art will recognize that the linker can be modified so as to provide different rates of hydrolysis varying from rapid to practically zero by altering the steric accessibility of the ester carbonyl carbon or by changing the chemistry to an amide linkage. Completely stable linker moieties can also be used which are free from potential hydrolytic degradation.

Synthesis and Analysis of BKAn/NEI Heterodimers

The synthesis of these compounds is illustrated by reference to Synthetic Schemes 2 and 3 and the following detailed synthesis description which includes the preparation of the elastase inhibitor CE-1218 according to Synthetic Scheme 1:

SYNTHETIC SCHEME 1

Synthesis of 4-tert-Butylacetophenone (1)

To a dry 1-L flask was added $CS_2$ (250 mL) and $AlCl_3$, (133.34 g, 0.56 mol) with stirring. The suspension was cooled in an ice bath and a solution of tert-butylbenzene (50.00 g, 0.37 mol) and acetyl chloride (78.50 g, 0.41 mol) was added dropwise over 2 hr (not allowing the temperature to rise above 25° C.). The reaction was allowed to stir at room temperature overnight and then poured into a 2 L beaker filled with ice. After quenching with 200 mL of 6 N HCl the solution was saturated with NaCl and separated. The aqueous layer was washed with ether (2×100 mL) and combined with previous organics. This new organic solution was washed with water (100 mL), dried ($MgSo_4$) and evaporated to give an oil which was distilled to give 52.1 g (79.3%) of 4-tert-acetophenone as a clear colorless oil ($bp_{0.05}$ mm 70–76° C.). $^1$H NMR ($CDCl_3$) δ 1.35 (s, 9 H), 2.58(s, 3 H), 7.48 (d, J=8.5 Hz, 2 H), 7.91 (d, J=8.5 Hz, 2 H). $^{13}$C NMR ($CDCl_3$) δ 26.42, 30.96, 34.95, 125.36, 128.16, 134.49, 156.64, 197.61.

Synthesis of Methyl 4-tert-butylphenylacetate (2)

A dry 1 L flask equipped with a mechanical stirrer containing $Pb(OAc)_4$ (132.06 g, 0.298 mol) and 250 mL of benzene was purged with nitrogen and cooled in an ice bath. To this cooled slurry was added dropwise a solution of $BF_3OEt_2$ (137.8 mL, 1.12 mol), 4-tert-butylacetophenone (50.00 g, 0.284 mol) in 70 mL of methanol over 1 hr. This mixture was allowed to stir overnight, quench with water (500 mL), diluted with 250 mL ether and the layers separated. The organic layer was washed with water, diluted $NaHCO_3$ (carefully) and dried over $MgSO_4$. The mixture was filtered, evaporated and distilled to give 31.2 g (53.4%) of methyl 4-tert-butylphenylacetate as clear colorless oil ($bp_{0.04}$ mm 75–80° C.). $^1$H NMR ($CDCl_3$) 1.32 (s, 9 H), 3.62 (s, 2 H), 3.71 (s, 3 H), 7.23 (d, J=8.4 Hz, 2 H), 7.37 (d, J=8.4 Hz, 2 H). $^{13}$C ($CDCl_3$) 31.33, 34.46, 40.67, 52.04, 125.53, 128.88, 130.91, 149.94, 172.26.

Synthesis of Methyl 4-tert-butylphenylisobutyrate (3)

A solution of methyl 4-tert-butylphenylacetate (30.00 g, 0.145 mol) and iodomethane (45.41 g, 0.320 mol) in 125 mL of dry THF was added to a slurry of NaH (8.72 g, 0.363 mol) in 200 mL of THF dropwise over 30 minutes. After completion of the addition, the reaction mixture was heated at reflux for 1.5 hr. The reaction was allowed to cool to room temperature, filtered through Celite and concentrated. The residue was diluted in ether, washed with H₂O, and dried over MgSO₄. Evaporation of the solvent afforded the desired product as an oil. A mixture of the crude methyl 4-tert-butylphenylisobutyrate and 4:1 EtOH/H₂O containing KOH (10.07 g, 0.179 mol) were heated to reflux for 4 hr. The EtOH was evaporated in vacuo, the residual solution was acidified to pH 2 with 2 N HCl, and the precipitated solid filtered. The white solid was the dried (60° C., 1 mm Hg, 24 hr) to give the desired product (23.45 g, 73.2% from methyl 4-tert-butylphenylacetate). ¹H NMR (CDCl₃) 1.34 (s, 9 H), 1.62 (s, 6 H), 7.37 (s, 4 H), 11.4–12.4 (brs, 1 H). ¹³C NMR (CDCl₃) 26.16, 31.30, 34.35, 45.81, 125.31, 125.48, 140.64, 149.66, 183.57.

Synthesis of 4-(3'-carbo-tert-butoxy-propyl mercapto) phenyl 4-tert-butylphenylisobutyrate (4)

A mixture of 4-tert-butylphenylisobutyric acid (2.00 g, 0.0091 mol) and thionyl chloride (1.62 g, 0.0136 mol) in 16 ml of CH₂Cl₂ was allowed to stir overnight under Argon. The volatiles were removed under vacuum and the resulting solid was dissolved into THF (15 mL) and a solution of tert-butyl-4-(4'-hydroxyphenyl)mercaptobutyrate (2.44 g, 0.0091 mol), TEA (2.5 mL) in THF (15 mL) was added dropwise over 10 min. The mixture was stirred for 3 days, diluted with Et₂O and extracted with 5% NaHCO₃. The organics were washed with H₂O, brine and dried (MgSO₄). After evaporization the colored oil was separated (HPLC, silica gel 70:30 CH₂Cl₂/hexane to CH₂Cl₂ linear graduent) to give the desired product as an oil (2.20 g, 51.5%). ¹H NMR (CDCl₃) δ 1.33 (s, 9 H), 1.43 (s, 9 H), 1.70 (s, 6 H), 1.88 (tt, J=7.2 Hz, 2 H), 2.35 (t, J=7.2 Hz, 2 H), 2.90 (t, J=7.2, 2 H), 6.92 (d, J=8.6 Hz, 2 H), 7.32 (d, J=8.6 Hz, 2 H), 7.34–7.40 (m, 4 H). ¹³C NMR (CDCl₃) δ 24.50, 26.42, 28.08, 31.31, 33.70, 34.11, 34.39, 46.40, 80.40, 121.92, 125.23, 125.46, 130.82, 133.03, 140.86, 149.58, 149.69, 172.21, 175.34.

Synthesis of 4-(3'-carboxy-propylmercapto)phenyl 4-tert-butylphenylisobutyrate (5)

Trifluoroacetic acid (25 mL) was added to a stirred solution of 4-(3'-carbo-tert-butoxy-propylmercapto)phenyl 4-tert-butylphenylisobutrate (2.40 g, 0.00510 mol) in 20 mL of CH₂Cl₂ over 15 min. After an additional 15 min the volatiles were removed and the oil crystallized (hexane) to give 1.94 g (91.8%) of desired product as a white solid, m.p. 86.0–87.0° C., ¹H (CDCl₃) 1.33 (s, 9 H), 1.70 (s, 6 H), 1.92 (tt, J=7.0 Hz, 2 H), 2.50 (t, J=7.0 Hz, 2 H), 2.93 (t, J=7.0 Hz, 2 H), 6.93 (d, J=8.7 Hz, 2 H), 7.33 (d, J=8.7 Hz, 2 H), 7.35–7.39 (m, 4 H). ¹³C NMR (CDCl₃) 23.89, 26.45, 31.32, 32.34, 33.63, 34.42, 46.42, 122.03, 125.24, 125.48, 131.12, 132.63, 140.85, 149.74, 175.40, 178.65.

Synthesis of 4-(3'-carboxy-propylsulfonyl)phenyl 4-tert-butylphenylisobutyrate (6)

To a 50 mL flask was added 4-(3'-carboxy-propylsulfonyl)phenyl 4-tert-butylphenylisobutyrate (1.64 g, 0.00396 mol), HOAc (25 mL) and 15 mL of 30% H₂O₂. The reaction was allowed to stir overnight, diluted with H₂O (50 mL) and the resulting solid filtered. After drying (12 hr, 1 mmHg) the solid was recrystallized (CH₂Cl₂/hexane) to give 1.54 g (87.1%) of the desired product as a white powder. mp 107–108.5° C. ¹H (CDCl₃) 1.33 (s, 9 H), 172.

(s, 6 H), 2.02 (p, J=7.0 Hz, 2 H), 2.52 (t, J=7.0 Hz, 2 H), 3.17 (t, J=7.0 Hz, 2 H), 7.20 (d, J=8.7 Hz, 2 H), 7.36 (d, J=8.7 Hz, 2 H), 7.41 (d, J=8.6 Hz, 2 H), 7.90 (d, J=8.6 Hz, 2 H). ¹³C NMR (CDCl₃) 17.88, 26.29, 31.28, 31.79, 34.42, 46.53, 55.04, 122.56, 125.16, 125.61, 129.70, 135.81, 140.22, 150.02, 155.29, 174.73, 177.71.

Synthesis of 6-Maleimidohexanol (7)

The synthesis of 6-maleimidohexanol to be used for linking is illustrated in Synthetic Scheme 2 below:

SYNTHETIC SCHEME 2

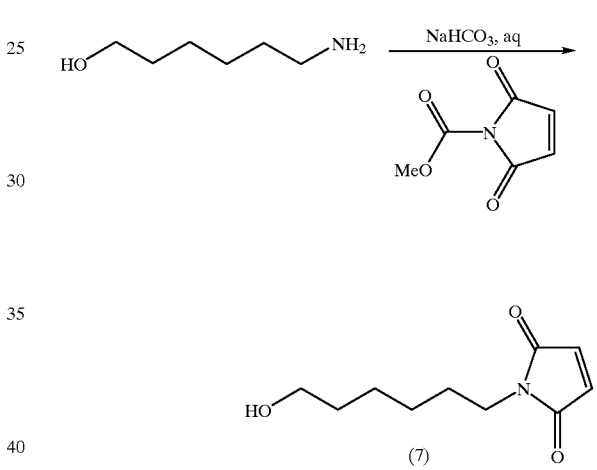

To a 100 mL flask was added 6-aminohexanol (0.76 g, 0.0064 mol) and 25 mL of saturated NaHCO₃. The homogenous was allowed to stir a RT and N-methoxycarbonylmaleimide (1.00 g, 0.0064 mol) was added as a solid. The mixture cleared shortly after the addition and was allowed to stir for 1 hr. The mixture was extracted by EtOAc, dried (MgSO₄) and evaporated. The resulting mixture was separated on silica gel (CH₂Cl₂ to EtOAC). To give the product as a white solid 0.32 g (25.2%), used without further purification. ¹H (CDCl₃) δ 1.25–1.45 (m, 4 H), 1.45–1.70 (m, 4 H), 3.53 (t, J=7.3 Hz, 2 H), 3.63 (t, J=6.0 Hz), 6.71 (s, 2 H).

Synthesis of CP-0502

Compound (6) (CE-1218) was esterified with compound (7) to form compound (8) which was then conjugated to CP-0126 to form the dimer CP-0502. These latter reactions are illustrated in Synthetic Scheme 3:

SYNTHETIC SCHEME 3

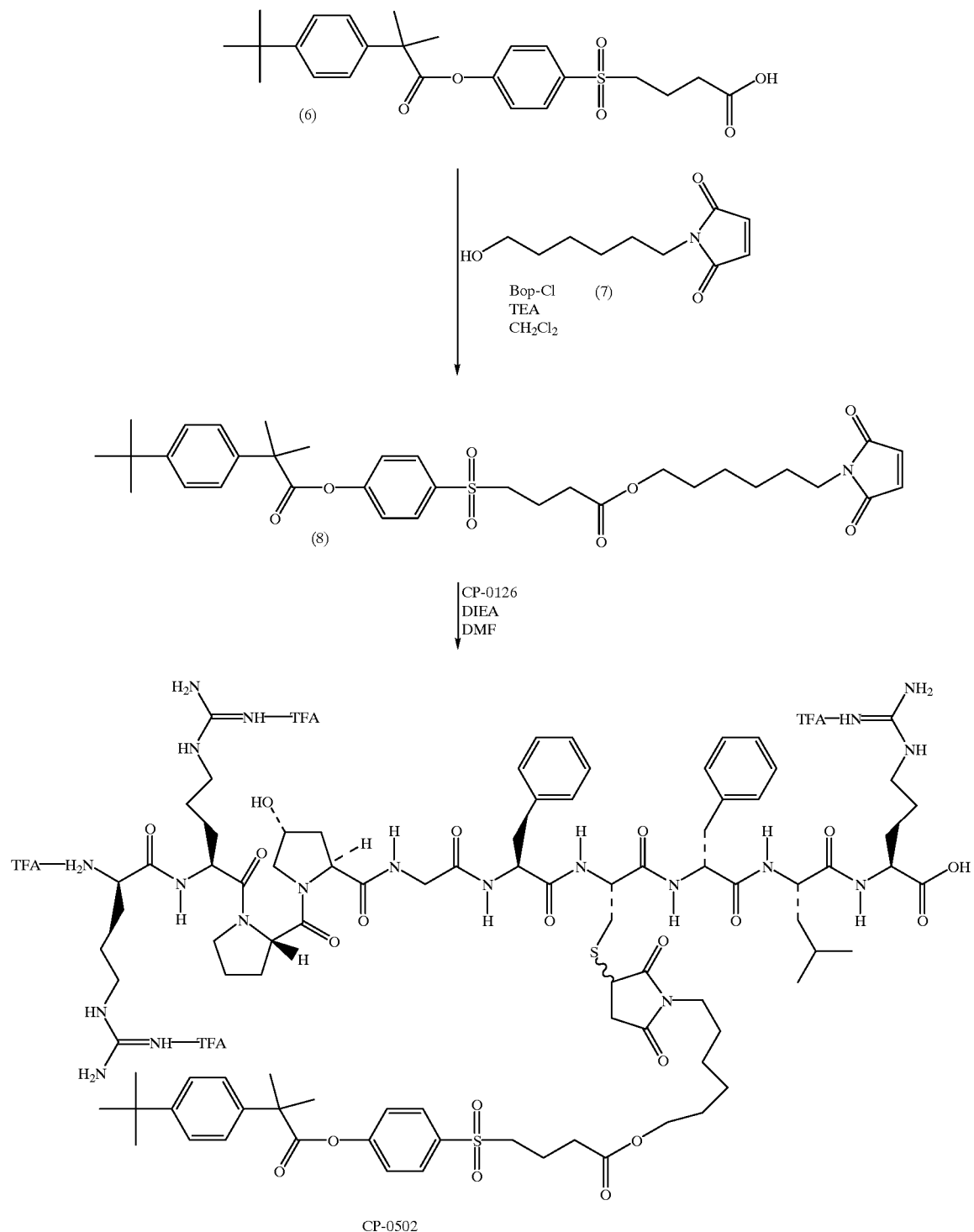

Referring more specifically to Synthetic Scheme 3, compound (6) (200 mg, 0.448 mmol), triethylamine (0.124 ml, 2 eqv), 6-maleimidohexanol (7) (97 mg. 1.1 eqv) were dissolved in 2 ml methylene chloride. Bis(2-oxo-3-oxazolidinyl) phosphinic chloride (122 mg, 1.0 eqv) was added to the stirred solution. The resulting suspension was stirred at room temperature for four hours. The reaction mixture was diluted with 25 ml methylene chloride and washed with saturated NaHCO₃. The organic solution was dried over anhydrous MgSO₄ and the solvent was removed in vacuo. Silica gel chromatography (2×18 cm column);

35/65:acetone/hexane (Rf=0.4) as eluent provided the compound (8) as a colorless oil.

Compound (8) (50 mg, 0.08 mmol) was dissolved in 10 ml DMF containing 100 ul diisopropylethylamine. 100 mg (0.08 mmols) of CP-0126 was added and reaction proceeded for 30 minutes, with occasional mixing. The reaction mixture was injected on a Vydac 1" C-18 reverse phase column, and eluted at 10 ml/min, 15%–90% acetonitrile in H2O over 35 minutes (Constant 0.1% TFA). The appropriate fractions were lyophilized to yield 52 mg (35%) of a colorless white powder (CP-0502) Laser desorption mass spectrometry M/Z=1890 (M+H), calculated 1890. Automated amino acid sequence results confirmed the correct peptide sequence with no altered amino acids.

In Vitro Activity of BKAn/NEI Heterodimer(s)

In vitro evaluation of BKAn and NEI activity of the following compounds was carried out according to standard protocols well known to those in the art. BKAn activity ($pA_2$) was assessed using the rat uterus preparation and NEI ($K_i^{ss}$) activity was evaluated using purified human neutrophil elastase (HNE) and a synthetic soluble chromogenic substrate, methoxysuccinyl-alanyl-alanyl-prolyl-valyl-paranitroaniline with (MOS-AAPV-pNA). The inhibitor was mixed with MOS-AAPV-pNA (0.5 mM) in 0.05 M sodium phosphate, 0.1 M NaCl, 0.005% Triton X-100, 5% DMSO, pH 7.5. HNE (10–20 nM) is then added. The production of nitroaniline was monitored spectrophotometrically at a wavelength of 400–410 nm at 25 C. An ENZFITTER program then automatically calculated standard enzyme kinetic parameters including $K_i^{ss}$.

The following results were obtained:

TABLE II

| Compound | $pA_2$—Rat Uterus | $K_i^{ss}$ (HNE) nM |
|---|---|---|
| CP-0126 | 7.1 | inactive |
| CE-1218 | inactive | 10.5 |
| CP-0487 | 8.4 | inactive |
| CP-0502 | 7.5 | 6.6 |

The data in Table II indicate that for NEI activity there is little difference between the intact heterodimer (CP-0502) and the free monomeric NEI moiety (CE-1218) as far as their respective $K_i$'s are concerned. This is not true for the activity of the BKAn portion of the intact heterodimer relative to its hydrolysis product, CP-0487 (the succinimidohexanol derivative of CP-0126) wherein the intact compound is almost a full log less potent than the monomeric BKAn. Interestingly, the activity of the intact compound displayed a type of irreversible bradykinin antagonism and an apparently enhanced antagonist activity of bradykinin induced uterine contractions at longer incubation times. These types of receptor interactions are not well measured by standard $pA_2$ analyses so the differences in activity observed between CP-0487 and CP-0502 with respect to BKAn activity may be more apparent than real. Regardless of the molecular pharmacologic mechanisms underlying these data it is clear that combined BKAn and NEI activity can be incorporated into a single molecule.

The above data suggest that allowing for in vivo hydrolysis of the intact compound may alter the behavior of the two moieties so as to enhance the overall in vivo activity of the primary compound. Unfortunately, there are no established animal models that can be employed to assess combined BKAn and NEI activity in vivo. Therefore, in order to assess the potential for in vivo hydrolysis of the intact heterodimer, an in vitro "surrogate" system was employed wherein the parent heterodimer (CP-0502) was incubated with human plasma and the resulting metabolites analyzed by reverse phase HPLC.

CP-0502 was added to freshly obtained normal human plasma and allowed to incubate at 37° C. for varying amounts of time. At the designated time the samples were treated with acidified (0.1 N HCl) acetonitrile in order to precipitate the plasma proteins. Aliquots (75 ul) of the supernatents were then analyzed on a Vydac C-18 reverse phase HPLC column using 24% to 80% acetonitrile gradient in 0.1% TFA. The eluent was monitored at 214 nm.

Figure 5A:
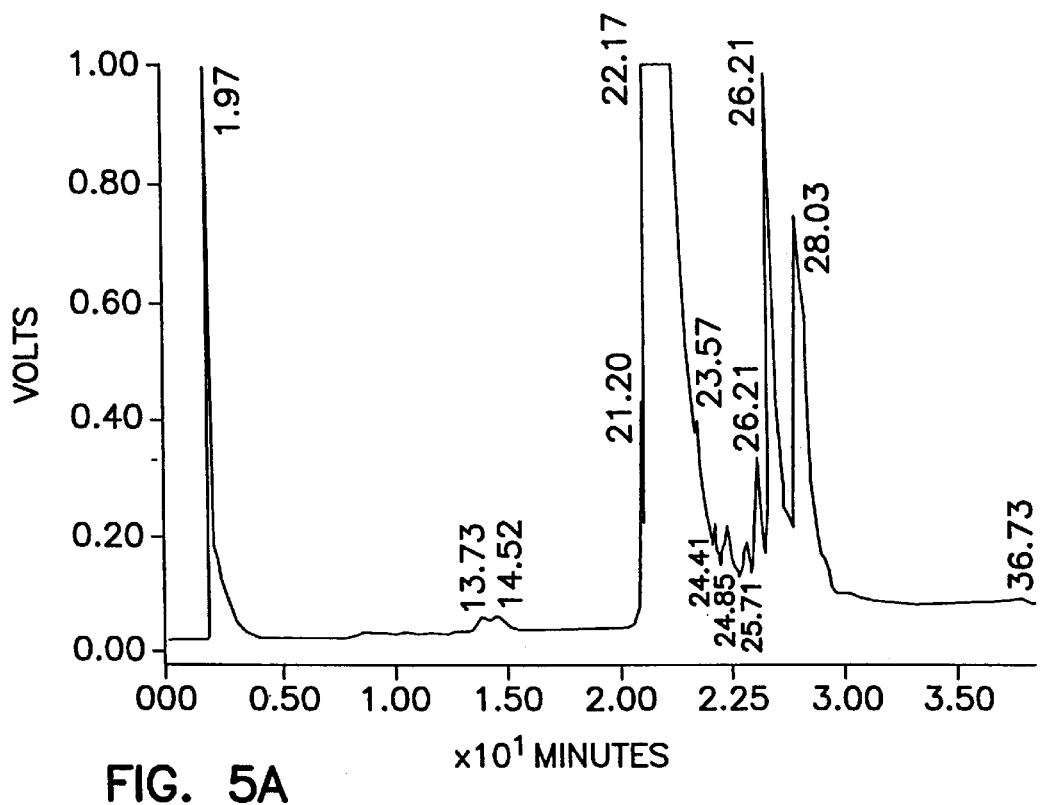
FIGS. 5A and 5B show the results of reverse phase HPLC analysis of metabolites after incubating compound CP-0502 with human plasma, followed by acid precipitation of plasma proteins.
Figure 5B:
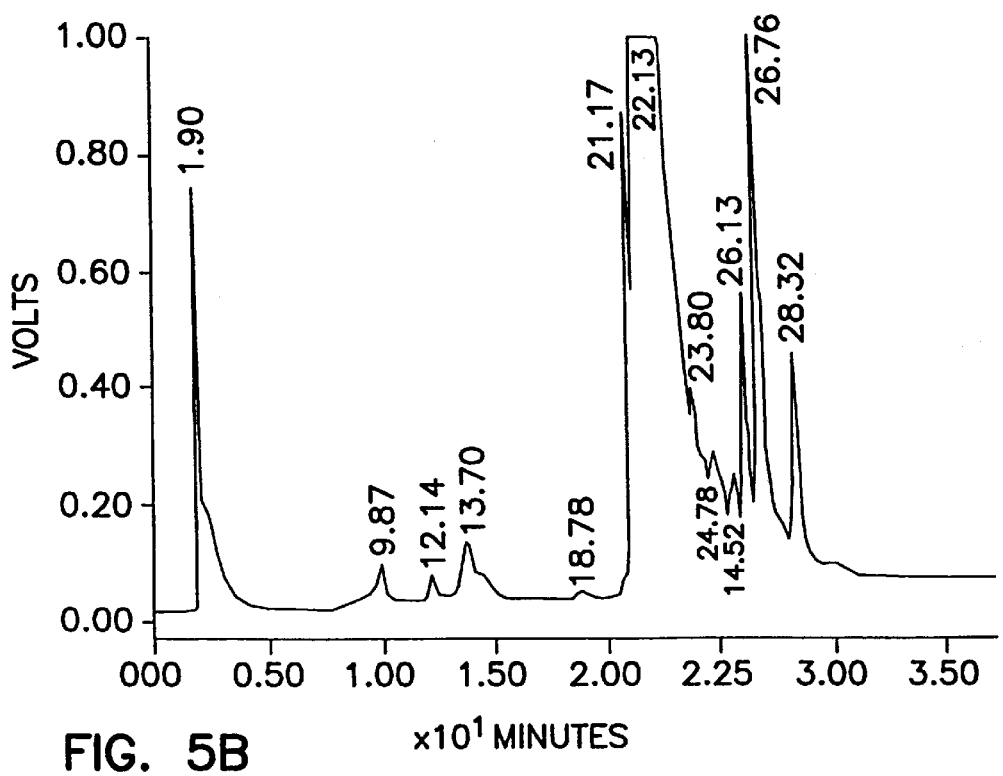

FIGS. 5a and b are representative reverse phase HPLC chromatograms illustrative of this type of analysis. As can be seen from these chromatograms, the parent compound appears to be readily hydrolyzed to the succinimidohexanol modified monomer, CP-0487 and its des-Arg⁹ derivative (Plasma carboxypeptidase will cleave the terminal arginine residue from both the intact heterodimer, CP-0502, as well as CP-0487.) The apparent $T_{1/2}$ of this hydrolysis reaction is approximately 113 minutes. The NEI component of the heterodimer is an active ester and undergoes hydrolysis as well. However, the intact NEI monomer as well as its hydrolysis products are obscured by the plasma derived peaks seen in the middle of this tracing and cannot be visualized using this system. Since the NEI is equally active as a component of the heterodimer as it is as a monomer, the dissociation of the heterodimer into its two component parts will have less of an effect on its activity than that for the BKAn component.

Those skilled in the art will appreciate that the hydrolysis rate of the heterodimer can be influenced by the steric and electronic environment of the "linking" ester moiety and that the type of chemistry used is only a single example of the types of chemistry that can be employed to adjust the rate of dissociation (or lack thereof) of the two components of the heterodimer.

EXAMPLE 6 (BKAn/COI)

Synthesis and Analysis of BKAn/COI Heterodimers

A representative BKAn/COI heterodimer (CP-0460) was synthesized according to Synthetic Schemes 4 and 5 below:

SYNTHETIC SCHEME 4

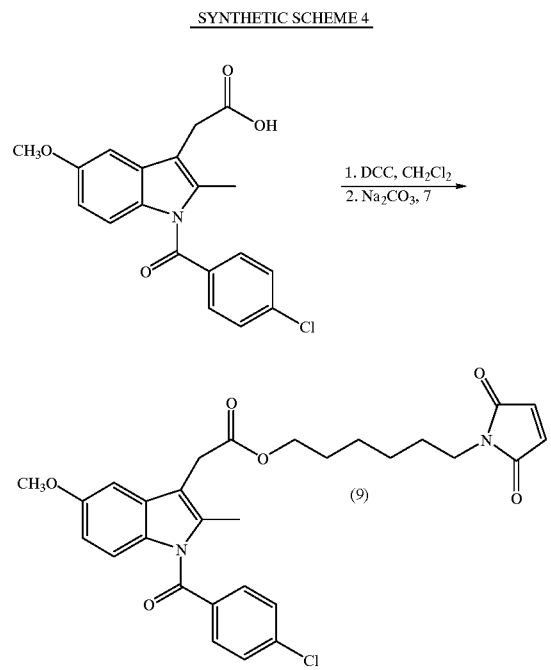

Synthesis of 6-Maleimidohexanyl 1-(4-chlorobenzoyl)-5-methoxy-2-methyl-3-indohylacetate (9)

To a 100 mL flask was added indomethacin (1.90 g, 0.00532 mol), 25 mL of $CH_2Cl_2$ and DCC (0.55 g, 0.00266 mol). After 2 hr, the mixture filtered, the DCU washed with 15 mL of $CH_2Cl_2$ and to this new solution was added 6-maleimidohexanol (0.50 g, 0.00253 mol) as a solid followed by anhydrous $Na_2CO_3$ (0.32 g, 0.00304 mol). After 4 days the mixture was filtered diluted with $Et_2O$ and washed with 5% $NaHCO_3$, $H_2O$ and dried $(MgSO_4)$. The resulting yellow oil was purified in a HPLC (silica gel; $CH_2Cl_2$ to 80:20 $CH_2Cl_2$/EtOAc, linear gradient 60 min.) to give 0.79 g (58.0%) of the desired product as a yellow oil. $^1H$ $(CDCl_3)$ 1.20–1.35 (m, 4 H), 2.38 (s, 3 H), 3.47 (t, J=7.3 Hz, 2 H), 3.66 (s, 2 H), 3.83 (s, 3 H), 4.08 (t, J=6.6 Hz, 2 H), 6.66 (J=9.0 Hz, J=2.5 Hz, 1 H), 6.68 (s, 1 H), 6.87 (d, J=9.0 Hz, 1 H), 6.96 (d, J=2.5 Hz, 1 H), 7.47 (d, J=8.5 Hz, 2 H) 7.66 (d, J=8.5 Hz, 2 H).

Conjugation of compound (9) with CP-0126 to form CP-0460 is illustrated in Synthetic Scheme 5 and described thereafter:

SYNTHETIC SCHEME 5

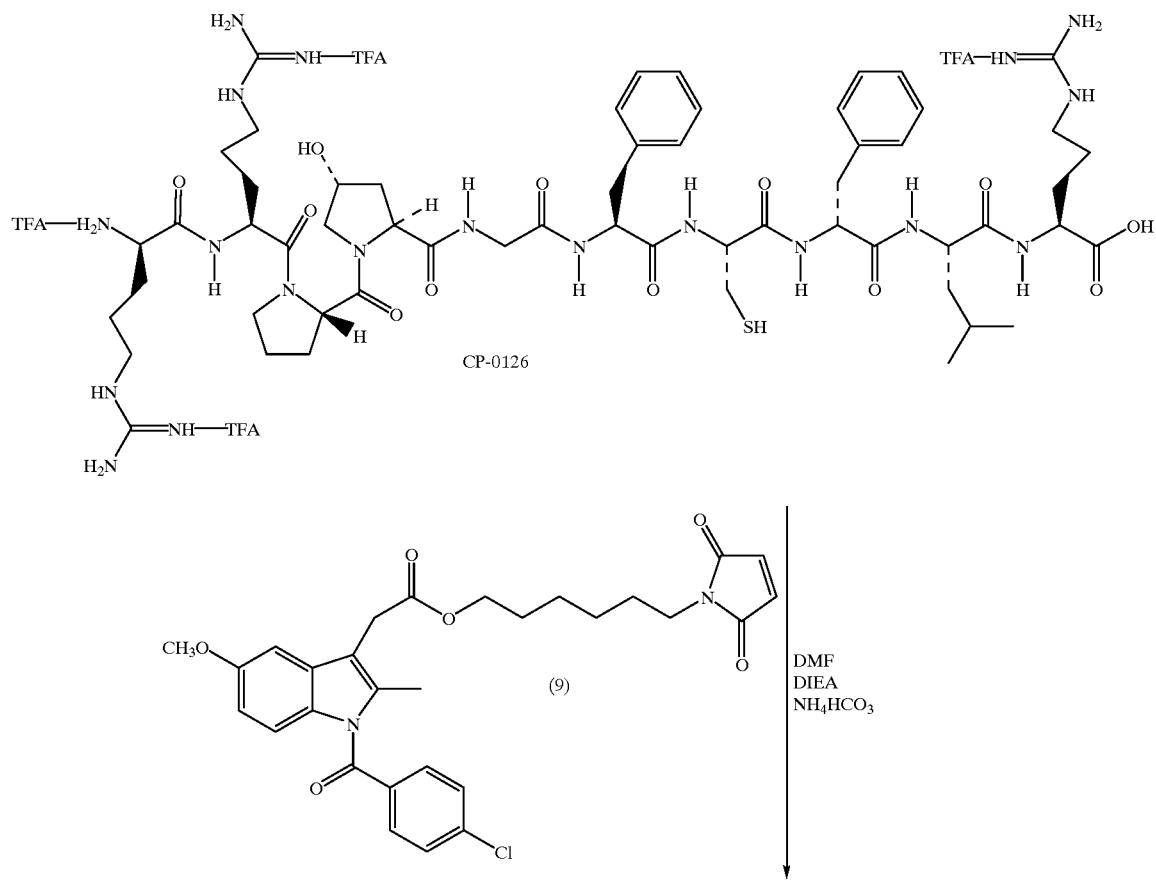

-continued

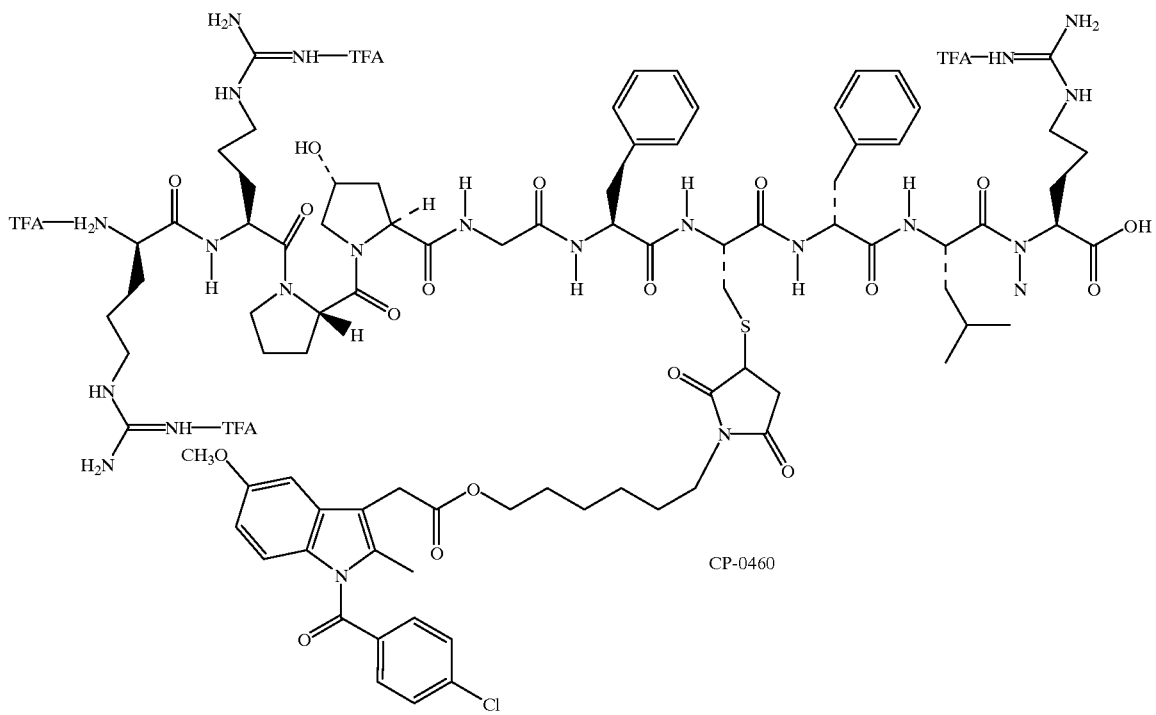

CP-0460

CP-0126 (100 mg, 0.08 mmol) was reacted with compound (9) (0.12 mmol, 1.5 eqv) in 2 mL 95% DMF/5% 0.1 M ammonium bicarbonate containing 50 ul diisopropylethylamine, for 30 minutes, with occasional mixing. The reaction mixture was purified in 1 injection on a Vydac 1" C-18 reverse phase column at 10 ml/min, using a gradient running from 15% acetonitrile/0.1% TFA to 40% acetonitrile/0.1% TFA in 20 minutes. Appropriate fractions were lyophilized to yield 64 mg (45%) of a colorless powder (CP-0460). Laser desorption mass spectrometry: M/Z=1,802 (M+H), calculated 1,802.

As mentioned previously, for the COI to work it may need to be dissociated from the BKAn so as to allow for its intracellular penetration. Therefore, in order to evaluate the functional activity of a BKAn/COI heterodimer, CP-0460 was exposed to rat lung parenchymal strips which were then challenged with arachidonic acid. This tissue is known to contain both non-specific esterase activity as well as to convert arachidonic acid to thromboxane (via a cyclooxygenase dependent pathway) which is then ultimately responsible for the smooth muscle contraction observed in this assay.

Using this system, the log dose ratio shifts for indomethacin and CP-0460 were found to be 0.998±0.425 and 1.029±0.042 respectively indicating that both indomethacin alone and CP-0460 will prevent the contraction produced in response to exogenously applied arachidonic acid with equal potency. BKAn's have no effect on this system in and of themselves. These data indicate that the COI component of BKAn/COI heterodimer is functionally active in a tissue containing both esterolytic and cyclooxygenase activities.

Intact CP-0460 was also tested for BKAn activity using the standard rat uterus assay and the $pA_2$ of the CP-0460 was found to be approximately 7.8. Again, CP-0460 (similarly to CP-0502) did not behave as a classical competitive antagonist of bradykinin induced uterine contraction but rather as a type of "pseudo-non-competitive" antagonist, particularly at higher concentrations. This atypical behavior cannot be attributed to COI activity per se as free indomethacin has no effect on this assay at any concentration.

Regardless of the explanation for the observed data, one skilled in the art will appreciate that, as in the other two classes of compounds illustrated herein, pharmacologically important BKAn/COI heterodimers can be made using a variety of appropriate linking moieties to provide a free hydroxyl and the carboxyl group (a common feature of many COIs) of the COI monomer to form a hydrolyzable ester based heterodimer. Compounds such as these may be used in the treatment of a variety of inflammatory or painful conditions as well as in the treatment of dysfunctional uterine smooth muscle activity.

While the invention has been exemplified above by the use of Y components which are non-peptides, this component may equally comprise in whole or part a peptide as exemplified in the afore-mentioned Ser. No. 07/859,582 and Ser. No. 07/677,391, the entire contents of these applications, including the heterodimers there described, being incorporated herein as earlier noted.

The dimers of the invention may be used in the form of conventional pharmaceutical compositions comprising the active component and a pharmaceutically acceptable carrier. Such compositions may be adapted for topical, oral, aerosolized, intramuscular, subcutaneous or intravenous administration. The amount of active component present in such compositions will range from, for example, about 0.001 to 90.0% by weight depending on the application and mode of administration although more or less of the active component may be used. Conventional dosages will vary considerably on the basis of the intended application and mode of administration. Usually, however, an effective dose is in the order of 0.1 to 1000 micrograms per kg body weight.

The scope of the invention is defined in the following claims wherein:

What is claimed is:

1. A heterodimer of the formula:

(BKAn)(X)(Y)

where BKAn is a bradykinin antagonist peptide; Y is selected from the group consisting of a neutrophil elastase inhibitor, a cyclooxygenase inhibitor, a $NK_1$ receptor antagonist, and a $NK_2$ receptor antagonist; and X is a linking group chemically joining the BKAn and Y components and said linking occurs via the amino acid residue in the 0, 1, 2, 3, 5, or 6 position of said BKAn.

2. A heterodimer according to claim 1, wherein Y is a neutrophil elastase inhibitor.

3. A heterodimer according to claim 1 wherein Y is a cyclooxygenase inhibitor.

4. A heterodimer according to claim 1, wherein Y is an $NK_1$ receptor antagonist or $NK_2$ receptor antagonist.

5. A heterodimer according to claim 1, wherein X is hydrolyzable.

6. A heterodimer according to claim 1, wherein X is non-hydrolyzable.

7. A heterodimer according to claim 1, wherein X comprises an amino acid or an amino acid analog incorporated into the BKAn.

8. A heterodimer according to claim 1, wherein X comprises a maleimide/succinimide-based linkage.

9. A heterodimer according to claim 1, wherein X comprises a bissuccinimidoalkane.

10. A heterodimer according to claim 1, wherein the BKAn comprise a cysteine residue in the 6-position; and wherein X forms a linkage through the —S— atom of the $Cys^6$ sulfhydryl group of the BKAn.

11. A heterodimer according to claim 1, wherein Y is a neutrophil elastase inhibitor, the BKAn comprise a cysteine residue in the 6-position, and X includes a succinimide group attached to the BKAn through the sulfur atom of the $Cys^6$ sulfhydryl group of the BKAn.

* * * * *